United States Patent [19]

Takehana et al.

[11] Patent Number: 4,930,494

[45] Date of Patent: Jun. 5, 1990

[54] APPARATUS FOR BENDING AN INSERTION SECTION OF AN ENDOSCOPE USING A SHAPE MEMORY ALLOY

[75] Inventors: Sakae Takehana, Hachioji; Yasuhiro Ueda, Kokubunji; Masakazu Gotanda, Tsukui; Tomohisa Sakurai; Hideyuki Adachi, both of Hachioji, all of Japan

[73] Assignee: Olympus Optical Co., Ltd., Tokyo, Japan

[21] Appl. No.: 291,242

[22] Filed: Dec. 28, 1988

[30] Foreign Application Priority Data

Mar. 9, 1988 [JP] Japan .................................. 63-53759
Mar. 28, 1988 [JP] Japan ............................. 63-73827[U]
Apr. 13, 1988 [JP] Japan ............................. 63-91093[U]
Apr. 13, 1988 [JP] Japan ............................. 63-91094[U]
Apr. 21, 1988 [JP] Japan ............................. 63-99040[U]
May 19, 1988 [JP] Japan ............................. 63-65140[U]
Jun. 2, 1988 [JP] Japan ............................ 63-136441[U]
Nov. 17, 1988 [JP] Japan ................................ 63-150069
Nov. 24, 1988 [JP] Japan ........................... 63-296803[U]

[51] Int. Cl.[5] .............................................. A61B 1/00
[52] U.S. Cl. ........................................ 128/4; 128/657
[58] Field of Search ................. 128/4, 6, 657; 604/95

[56] References Cited

U.S. PATENT DOCUMENTS

| 4,054,128 | 10/1977 | Seufert et al. ........................ 128/4 |
| 4,182,547 | 1/1980 | Siegmund ........................... 128/4 X |
| 4,427,000 | 1/1984 | Ueda .................................... 128/6 |
| 4,543,090 | 9/1985 | McCoy ........................... 128/657 X |
| 4,601,283 | 7/1986 | Chikama ............................... 128/4 |
| 4,742,817 | 5/1988 | Kawashima et al. ................. 128/4 |
| 4,799,474 | 1/1989 | Ueda ..................................... 128/4 |

FOREIGN PATENT DOCUMENTS

| 0199870 | 5/1986 | European Pat. Off. . |
| 58-25140 | 2/1983 | Japan . |
| 58-101601 | 7/1983 | Japan . |
| 59-2344 | 1/1984 | Japan . |
| 59-48710 | 3/1984 | Japan . |
| 59-177777 | 11/1984 | Japan . |
| 60-26181 | 2/1985 | Japan . |
| 60-53234 | 3/1985 | Japan . |
| 60-175777 | 9/1985 | Japan . |
| 61-46475 | 3/1986 | Japan . |
| 61-63482 | 4/1986 | Japan . |
| 61-92588 | 6/1986 | Japan . |
| 61-94001 | 6/1986 | Japan . |
| 61-175278 | 8/1986 | Japan . |
| 61-255669 | 11/1986 | Japan . |
| 61-201018 | 12/1986 | Japan . |
| 63-136014 | 6/1988 | Japan . |

OTHER PUBLICATIONS

"Study on the Shape Memory Alloy Actuator", No. 10 Considerations on Optimus Conditions of SMA and Realization of Real Scale Active Endoscope, Tokyo Institute of Technology; S. Hirose et al.

Primary Examiner—William H. Grieb
Attorney, Agent, or Firm—Frishauf, Holtz, Goodman & Woodward

[57] ABSTRACT

The distal end of an insertion section of an endoscope is divided into a plurality of segments each including a pair of SMA coils which are arranged symmetrically with respect to an axis and memorize a close-winding shape. As the SMA coils recovers their memorized shape, the distal end of the insertion section is bent. The SMA coils are restored to the memorized shape when they are conductively heated by means of a current supply circuit. The current supply circuit comprises an input unit for inputting a target value of the bend angle for a leading segment, a sensor for detecting the distance of insertion of the insertion section, a detector circuit for detecting the bend angle of each segment, and means for controlling the amount of current supply so that the bend angle of the SMA coils agrees with a target angle. The inputted angle is set as the target angle for the leading segment, and the detected bend angle of each segment is set as the target angle for each succeeding segment. The set value is renewed each time the insertion distance of the insertion section attains a predetermined distance.

37 Claims, 29 Drawing Sheets

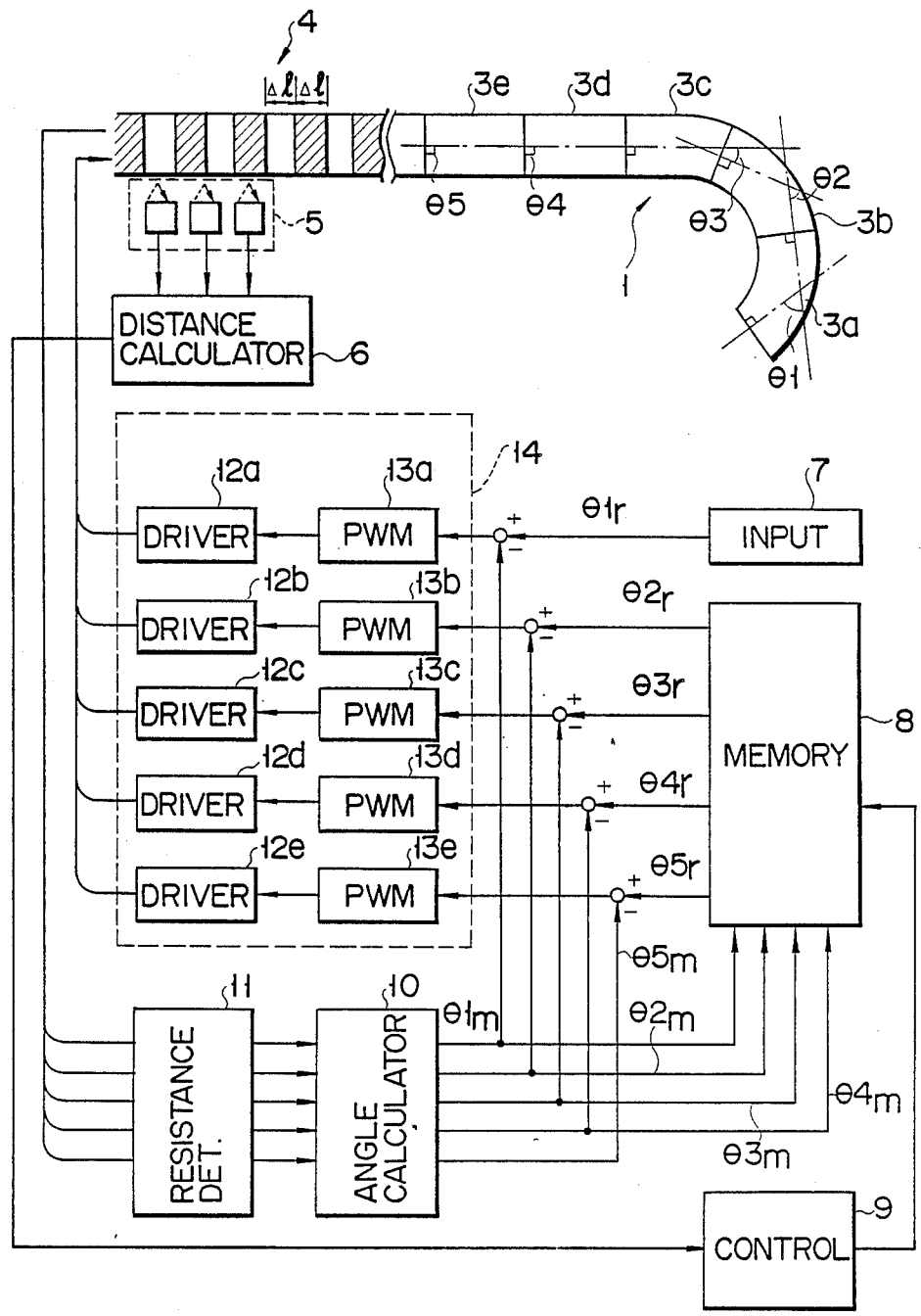
F I G. 1

FIG. 5
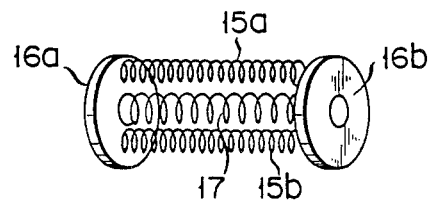
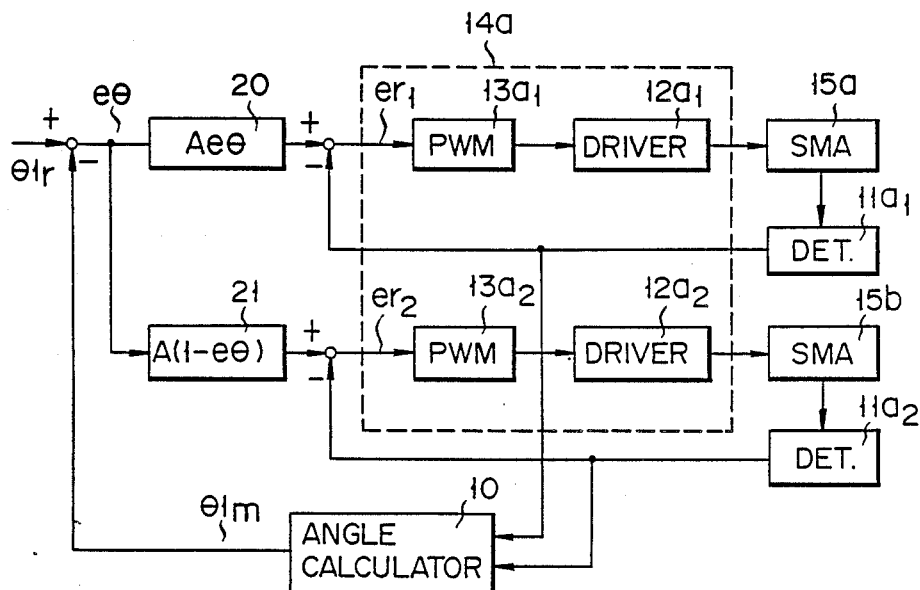
FIG. 6

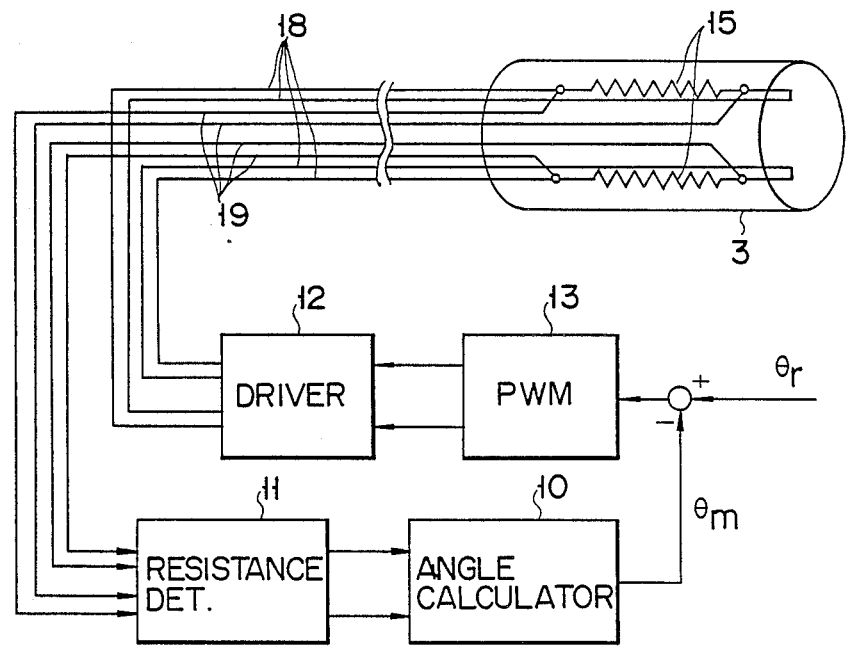
F I G. 9

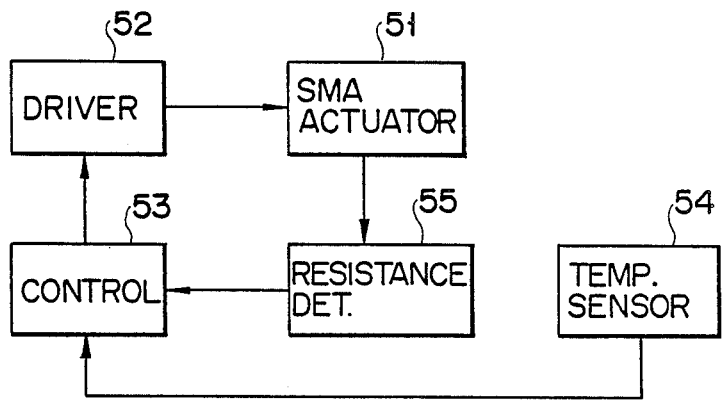
FIG. 20
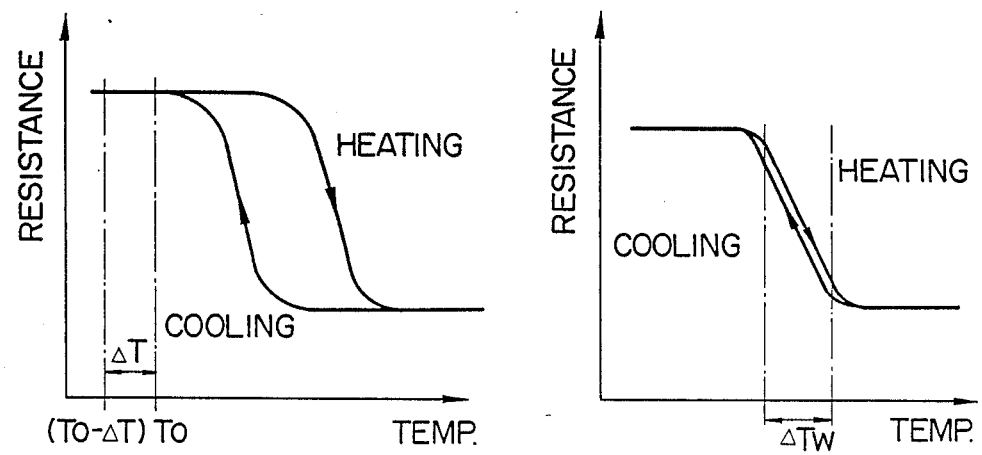
FIG. 21
FIG. 22

(OFF)
  (OFF)
  (OFF)
  (OFF)
FIG. 26A ─────────── (OFF)
FIG. 26B ─────────── (OFF)
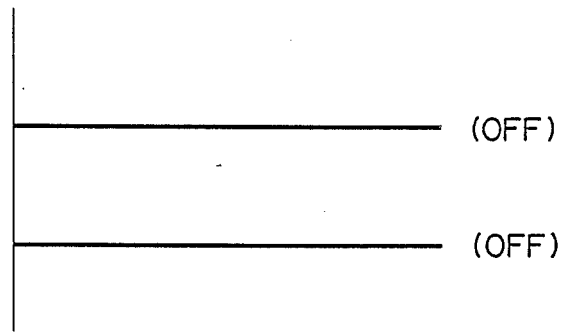

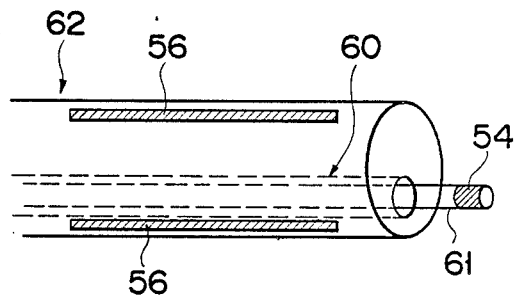
F I G. 27
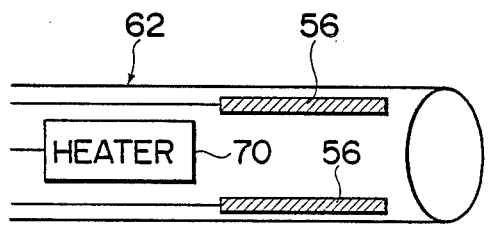
F I G. 28

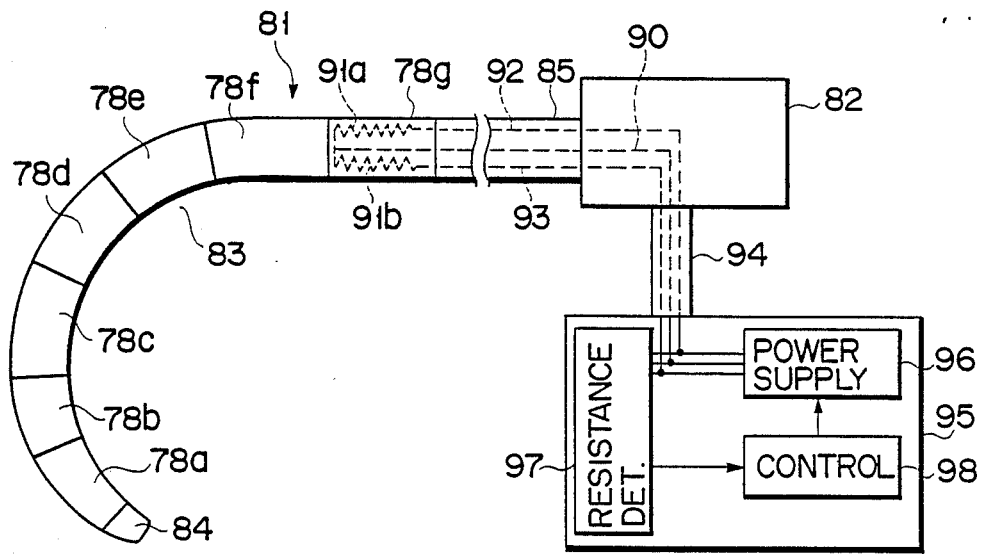
F I G. 29
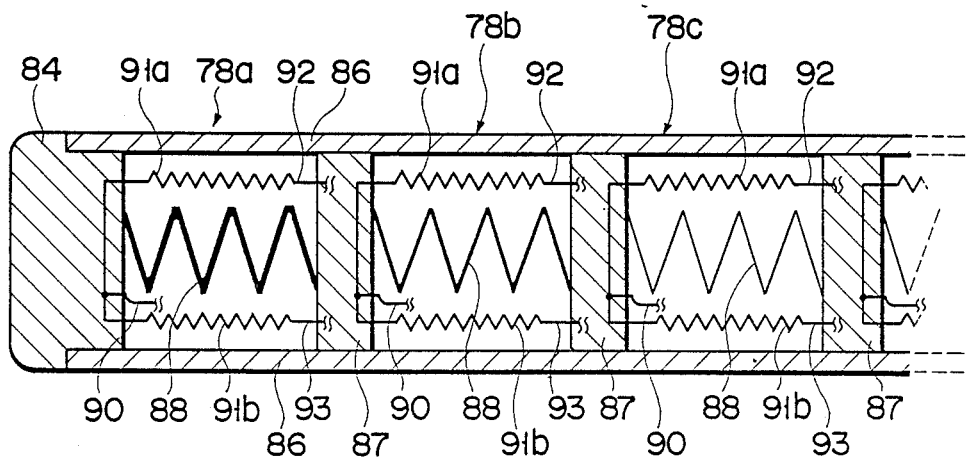
F I G. 30

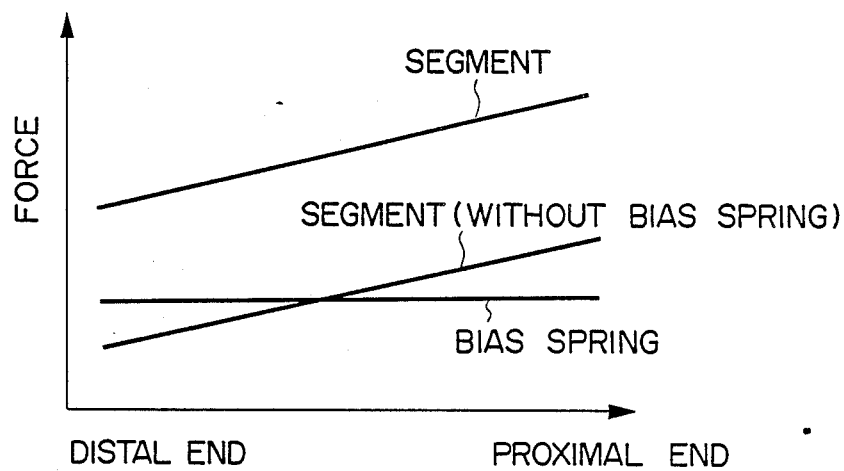
F I G. 31
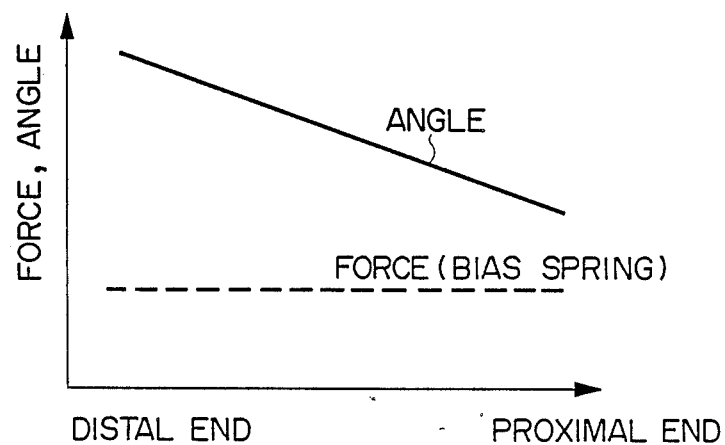
F I G. 32

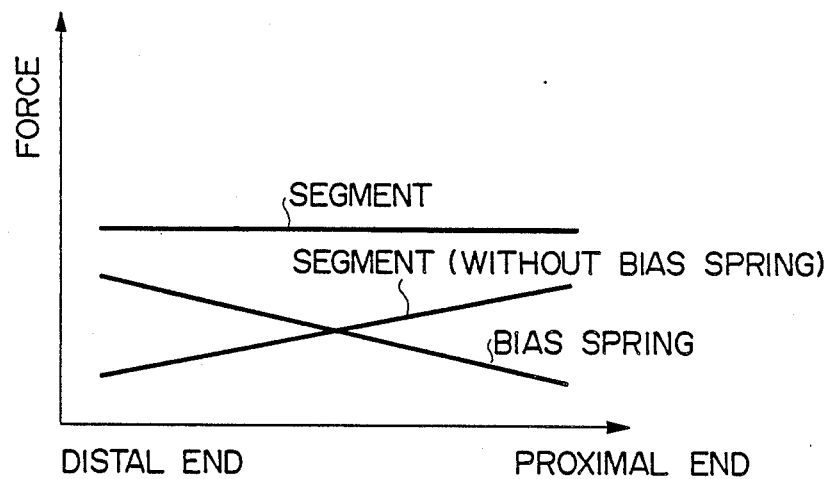
F I G. 33
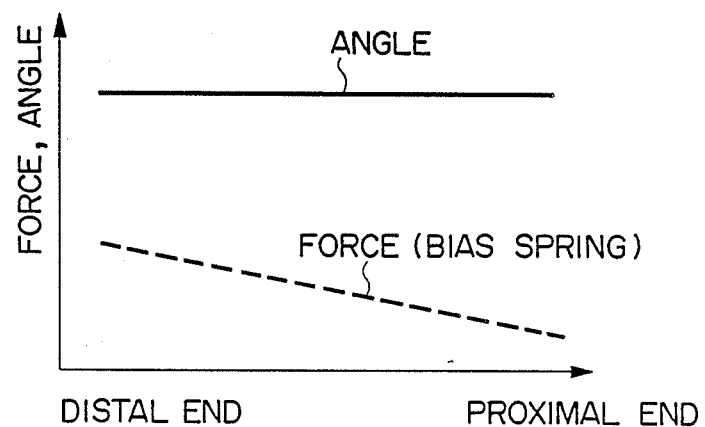
F I G. 34

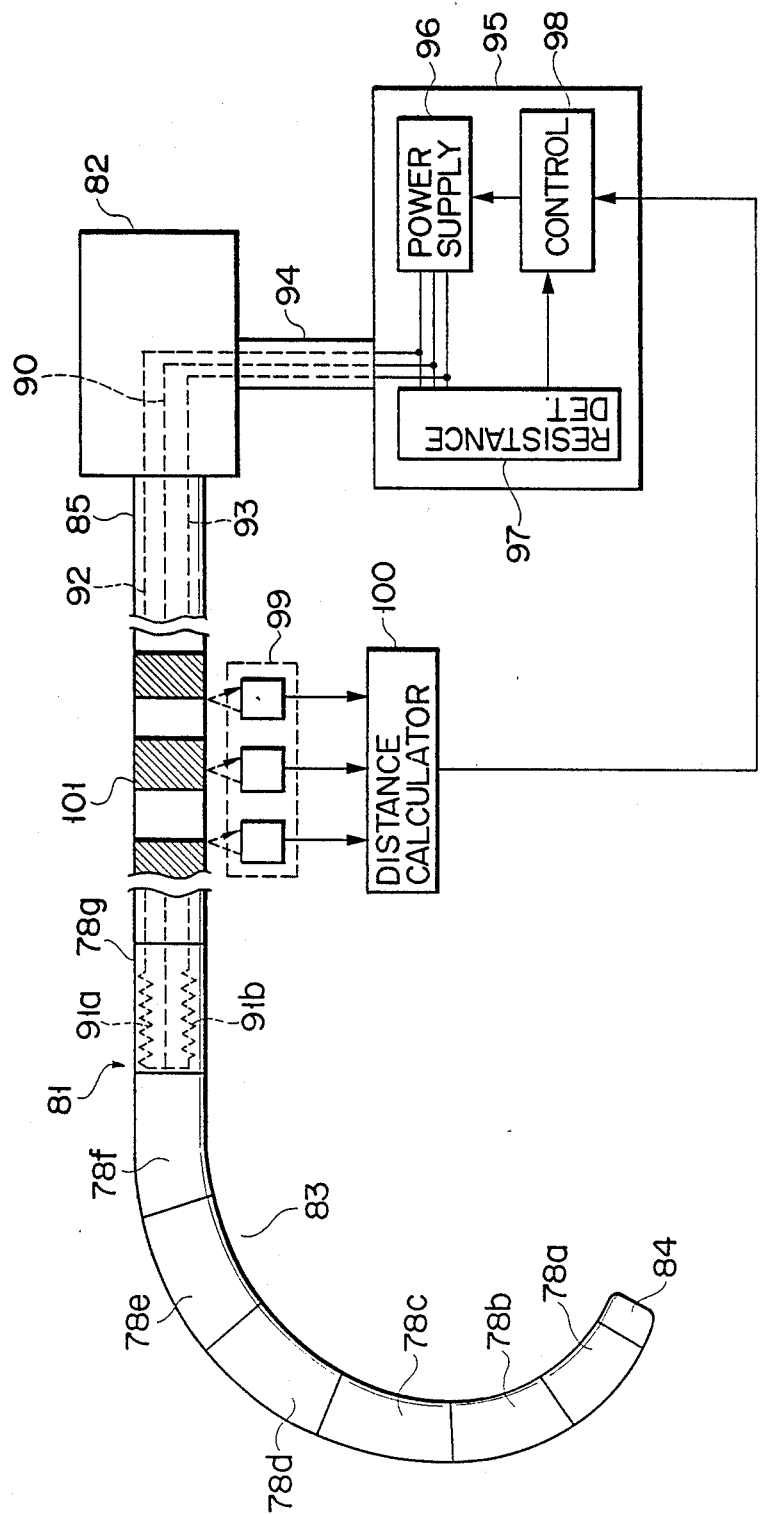
F I G. 35

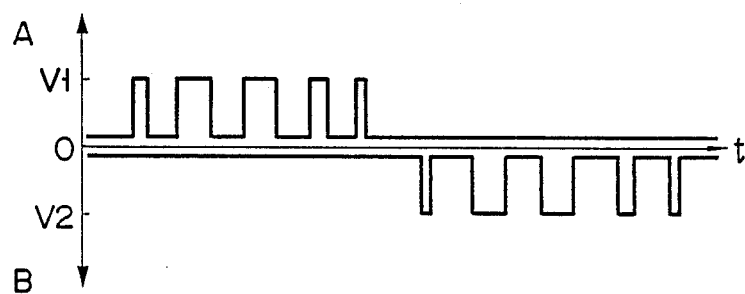
F I G. 38
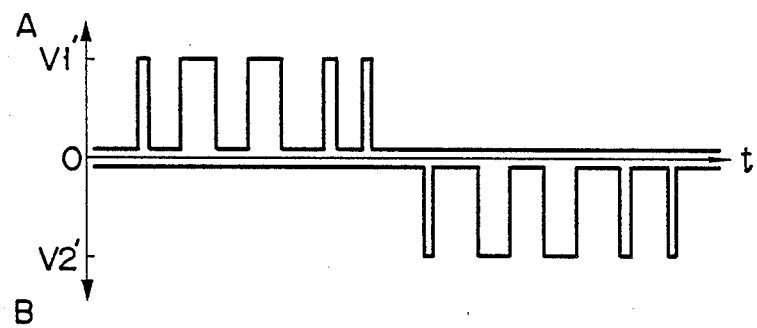
F I G. 40
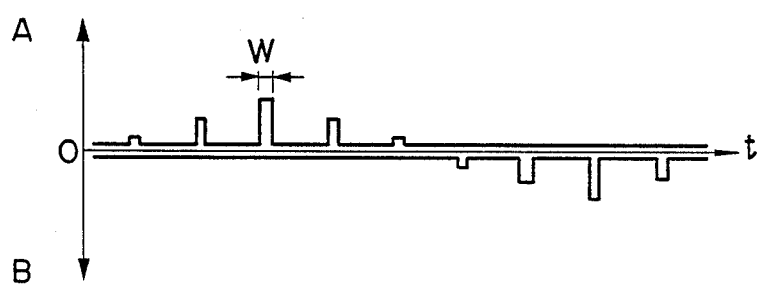
F I G. 42
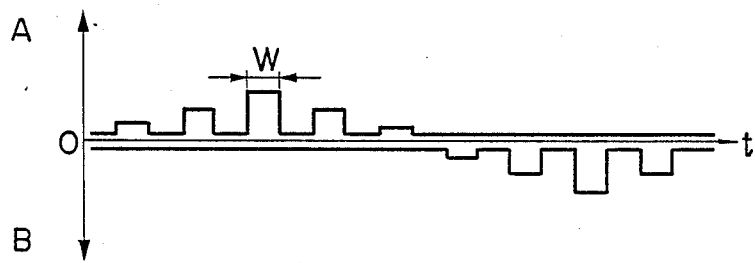
F I G. 43

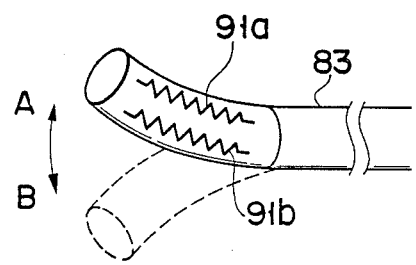
F I G. 39
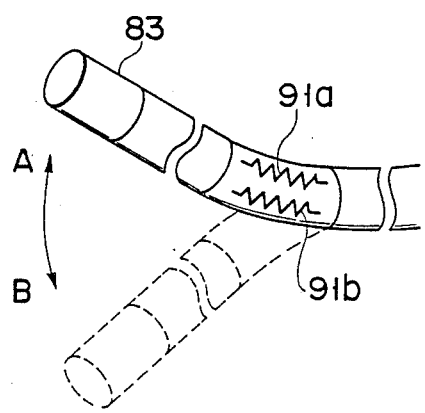
F I G. 41

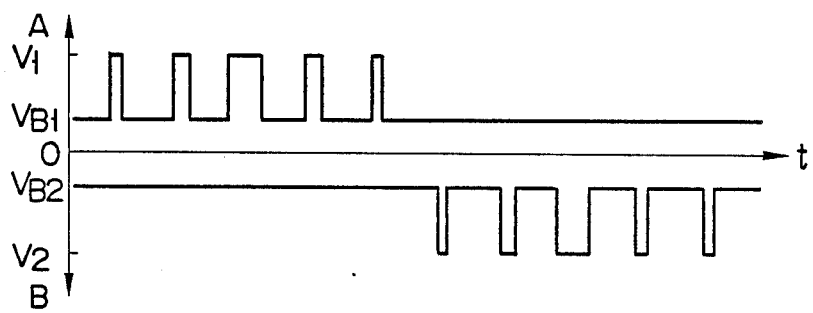
F I G. 44
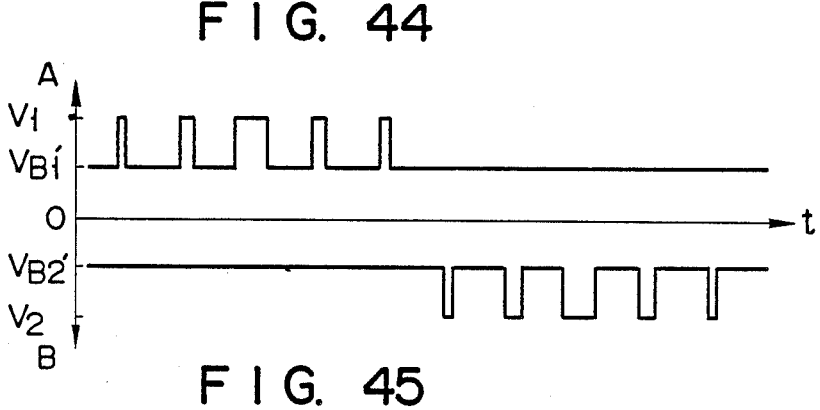
F I G. 45
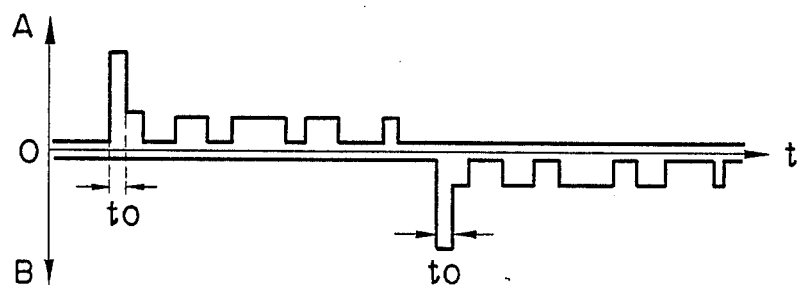
F I G. 46
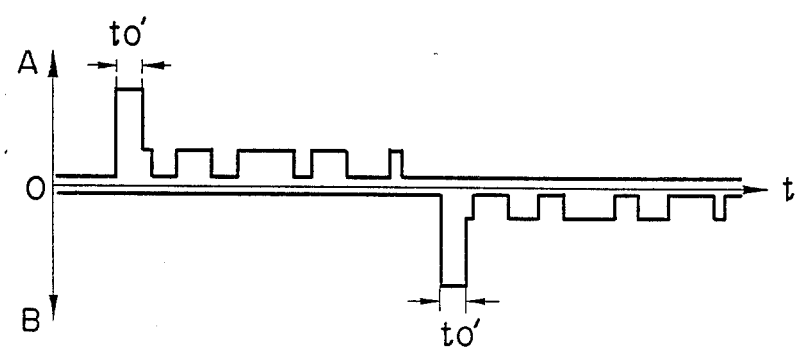
F I G. 47

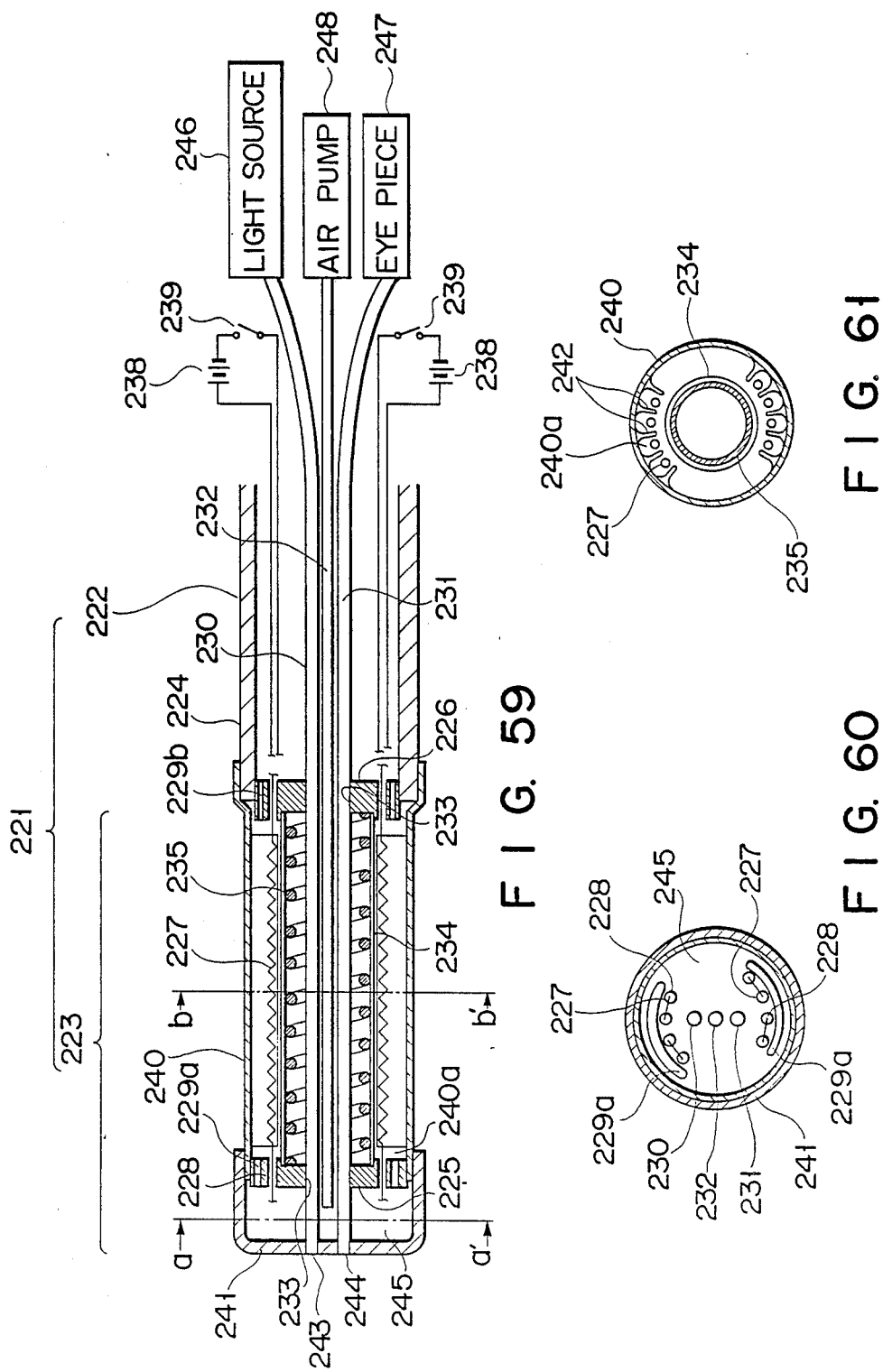

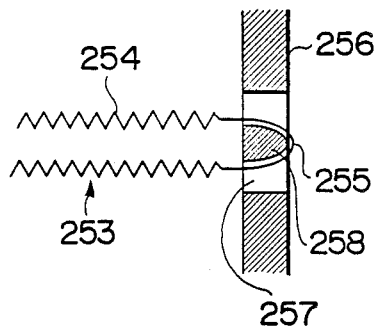
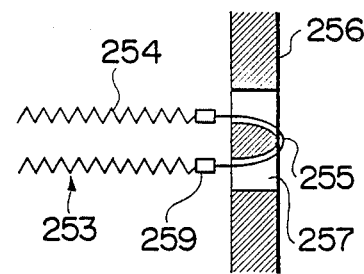
F I G. 66   F I G. 67
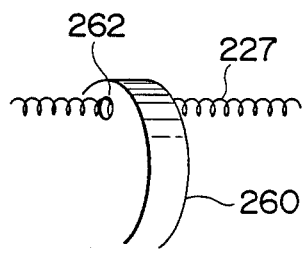
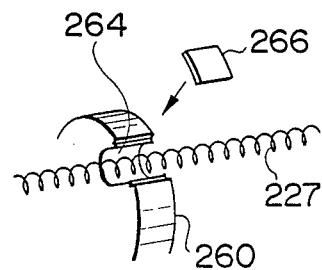
F I G. 68   F I G. 69

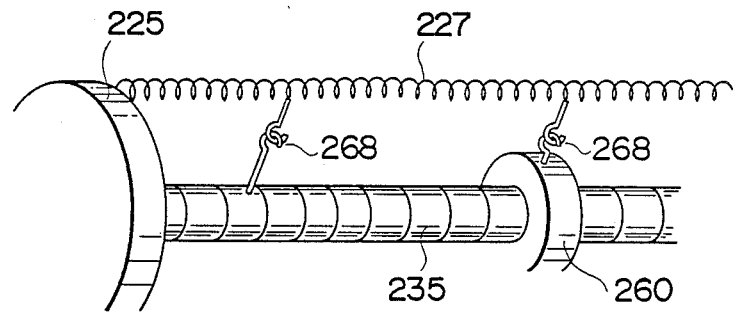
FIG. 70
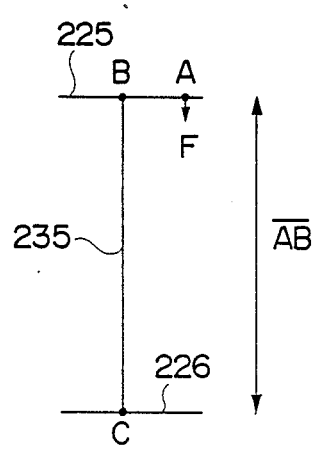 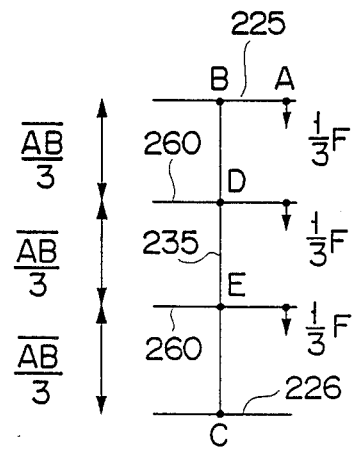
FIG. 71  FIG. 72

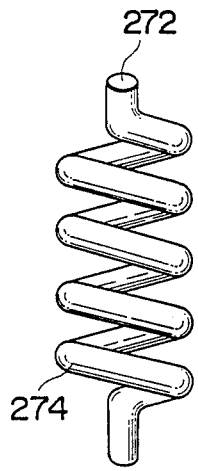
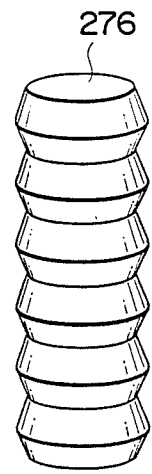
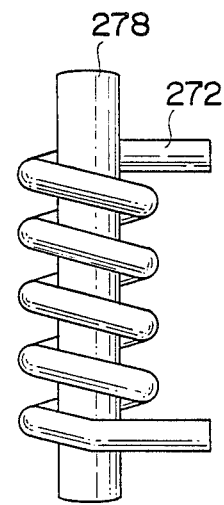
F I G. 73    F I G. 74    F I G. 75
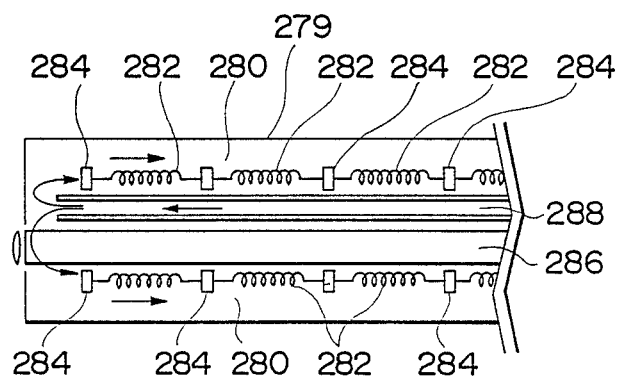
F I G. 76

APPARATUS FOR BENDING AN INSERTION SECTION OF AN ENDOSCOPE USING A SHAPE MEMORY ALLOY

BACKGROUND OF THE INVENTION

1. Field of the Invention

The present invention relates to a shape memory apparatus which operates for itself or drives loads and the like by utilizing changes of shape of a shape memory element, such as a shape memory alloy (hereinafter referred to as SMA), caused by temperature changes.

2. Description of the Related Art

As an example of the apparatus of this type, there is an apparatus which bends a tubular member, such as an endoscope or catheter, to insert it into an alimentary canal of a living body. In a conventional endoscope, wires are stretched over the full length of its insertion section, and their distal ends are connected to the distal end of a bending portion which is connected to the distal end of the insertion section, while the proximal ends are connected to a knob at a control section which is connected to the proximal end of the insertion section. The wires are loosed and pulled to bend the bending portion by turning the knob. In the case of an endoscope with a relatively long insertion section, e.g., an industrial endoscope, however, it is difficult to obtain a sufficient bend angle by this method because the wires tend to slacken substantially. Moreover, the insertion of the endoscope requires a great deal of skill, and the endoscope sometimes cannot be bent to an optimum angle when it is inserted into an alimentary canal of a complicated configuration, such as the large intestine.

In order to solve these problems, "Study of Servo Actuator Using Shape Memory Alloy" (Shigeo Hirose et al.) was proposed in the 4th Science Lecture Meeting of the Japan Robotological Society (No. 3406, 1986). In this proposed arrangement, the distal end of an insertion section of an endoscope is divided into a plurality of segments, each containing an SMA. The SMA or segment can be bent by heating the SMA with Joule heat to recover a memorized shape of the SMA.

The amount of current supply to the SMA of each segment for generating Joule heat is controlled as follows. First, an operator manually adjusts the amount of current supply to the SMA of the leading segment, while observing an image inside the canal obtained through an image guide fiber. Then, the bend angle of each segment is detected by detecting the resistance of the SMA. In synchronism with the insertion of the endoscope by a distance corresponding to the length of each segment, the detected bend angle is set as a target value of the bend angle for a subsequent segment. Thereafter, the amount of current supply to the segments succeeding the leading segment is controlled in accordance with each target value obtained in this manner. In other words, the bend angle of the leading segment is shifted as the control target value to succeeding segments.

In this conventional example, however, each succeeding segment can bend only to the same angle as the leading segment. When inserting the endoscope of this type into the large intestine or some other portion whose configuration varies as any substance is inserted thereinto, the difference between the respective configurations of the endoscope and the alimentary canal causes the latter to be subjected to an unreasonable force, thus entailing danger.

In the conventional SMA temperature control, the SMA is heated only when it is to be restored to its memorized shape, so that the minimum temperature of the heat cycle applied to the SMA is the environmental temperature (room temperature). If the As' (Austenite start)-point is high, as in the case of a Ti-Ni alloy, the difference between the maximum and minimum temperatures of the heat cycle becomes so great that the minimum temperature is not higher than Ms (Martensite start)-point. Thus, the fatigue life performance of the SMA will be lowered.

These drawbacks may be eliminated by the use of a shape memory alloy apparatus disclosed in Japanese Patent Disclosure No. 61-46475. According to this apparatus, the fatigue life performance of the SMA is improved by heat-biasing the SMA so that the temperature of the SMA is lower than the As'-point and higher than the Ms-point. More specifically, a constant bias current is applied when the recovery of the shape need not be effected. This bias current is set to a value such that the SMA is kept slightly under the As'-point when only the bias current is applied. If a current obtained by superposing a heating current (pulse current) on the bias current is applied, the SMA is heated above the As'-point, thereby recovering the memorized shape.

As described above, this prior art example is based on the assumption that the SMA can be kept slightly under the As'-point if it is supplied with the constant bias current. Actually, however, there is an influence of the environmental temperature (room temperature), so that the SMA cannot always be kept under the As'-point despite the supply of the constant bias current. Thus, the conventional example has no regard for the environmental temperature of the SMA, so that the responsiveness or accuracy may possibly be lowered. If the SMA is at a temperature below the normal working temperature range, for example, its resistance never changes despite a drop of the environmental temperature. Accordingly, the response speed will be lowered if feedback control is based only on the resistance. If the environmental temperature changes, the temperature-displacement characteristic of the SMA also changes, so that a desired displacement of the SMA sometimes cannot be obtained.

Disclosed in Japanese Patent Disclosure No. 58-25140, Japanese Utility Model Disclosure Nos. 58-101601, and 61-201018 and Japanese Patent Disclosure No. 59-48710 are endoscopes in which the SMA is contained in its insertion section to effect the bending action of the insertion section. However, these endoscopes are subject to the following drawbacks. In general, a long SMA cannot be shape-memorized. If each segment of the insertion section is independently expected to be bent over a relatively long range by means of the SMA, in order to facilitate insertion into a complicated alimentary canal, such as the large intestine, therefore, a number of shape memory elements must be mechanically connected in series. Thereupon, the individual SMAs elements must bend sustaining the weight of that portion of the insertion section on the distal end side. Thus, in bending all the segments to equal bend angles, the forces needed to bend the segments are greater with distance from the distal end. In other words, the load of the segments on the distal end side and the necessary bending forces therefor are smaller. Even though the SMAs in the individual segments are subjected to the same amount of heating, therefore, the bend angles can not be equalized, so that the insertion section cannot be subjected with uniform bending control.

Disclosed in Japanese Patent Disclosure No. 60-175777, moreover, is an example of a shape memory actuator in which load is driven by utilizing the thermodynamic energy exchanging function of the SMA. In this actuator, a moving part is supported on the underside of a fixed part by means of an SMA coil spring, which is connected to a power source. If the SMA coil spring is energized, it contracts to be restored to its memorized shape, by means of Joule heat produced by conductive heating, thereby raising the moving part. If it is cooled, the SMA coil spring extends, thereby lowering the moving part.

The fixed and moving parts are each provided with a through hole through which the SMA spring is passed, although they are not fixed to the spring. More specifically, the end portions and junctions of the SMA spring are passed through the holes and are bent or knotted.

Meanwhile, in the shape memory actuator, transformation of the SMA coil spring is transmitted to the moving part to operate it. In this case, the force of the SMA coil spring cannot be fully transmitted to the moving part by only passing the spring through the holes in the fixed and moving parts. Thus, the force produced by the SMA cannot be effectively utilized.

The response speed of the SMA is proportional to the periods of time required for heating and cooling the SMA. Therefore, it can be increased by minimizing these periods. In general, the SMA can be heated in a relatively short period of time. On the other hand, there are hardly any effective cooling means. For example, the cooling means for this purpose include ones which use a cooling fluid, such as air, or heat exchanging elements, such as Peltier elements. In the cooling means using the cooling fluid, the fluid must be uniformly circulated through SMA elements, so that each SMA element is contained in a cooling pipe, as described in Japanese Utility Model Disclosure 61-92588. This arrangement is well adapted for the case in which the shape recovering effect of the SMA is utilized for a linear motion. It cannot, however, be effectively used for bending operation. Thus, the elasticity of the cooling pipes constitutes a load on the bending operation. The bending force may be enhanced by thickening the wires of SMA springs or by increasing them in number. If this is done, however, the cooling pipes must be increased in diameter and in number. Thus, this arrangement cannot be easily applied to endoscopes.

SUMMARY OF THE INVENTION

The present invention has been contrived in consideration of these circumstances, and has an object to provide a shape memory apparatus which is adapted to bend according to the shape of a tubular member as it is inserted thereinto, and which can bend following variation of the shape of the tubular member so as to be smoothly inserted thereinto.

Another object of the invention is to prevent the responsiveness of shape memory elements in the shape memory apparatus described above from lowering, despite the change of environmental temperature.

Still another object of the invention is to uniformly drive and control any shape memory elements in the aforementioned shape memory apparatus, irrespectively of the conditions of location of the element.

A further object of the invention is to efficiently utilize a force generated by the shape memory elements when they recover their shape, in the aforementioned shape memory apparatus.

An additional object of the invention is to efficiently cool the shape memory elements, in order to restore the elements to their original state after the recovery of the memorized shape, in the aforementioned shape memory apparatus.

A shape memory apparatus according to the present invention comprises an insertion section composed of a plurality of flexible segments, each having a shape memory element and connected in series with one another. Each time the insertion section is moved in for a predetermined distance, the bend angle of each segment is detected. The detected bend angle of each segment is set as a target value of the bend angle for a subsequent segment with respect to the direction of movement. The temperature of each shape memory element is controlled so that the bend angle of each segment agrees with the target value.

In the shape memory apparatus according to the present invention, a temperature sensor is located beside each shape memory element, whereby the working environmental temperature of the element is detected. The drive amount of a driver circuit of the shape memory element, i.e., the amount of heating or cooling of the element, is adjusted in response to the detected temperature.

The shape memory apparatus according to the present invention comprises a bending portion including a plurality of series-connected segments, each having a shape memory element, and means for supplying a current to the shape memory elements to heat thereof, the current supplying means being connected to the bending portion. The segments are designed so that the ones on the distal end side are less easy to bend, that is, the ones on the proximal end side are easier to bend. Alternatively, the amount of current supply for the same target bend angle is made greater with distance from the distal end side.

In the shape memory apparatus according to the present invention, the shape memory element is fixed to flange members, which are provided ends of the segments, by means of fixing members.

In the shape memory apparatus according to the present invention, the shape memory element is disposed in a passage with internal knurls, and a cooling medium is circulated through the passage at the time of cooling.

In the shape memory apparatus according to the present invention, the surface of the shape memory element is colored for good heat radiation.

Brief Description of the Drawings

FIG. 1 is a block diagram of an endoscope to which is applied a first embodiment of a shape memory apparatus according to the present invention;

FIG. 5 is a schematic view of one segment of the insertion section of the first embodiment;

FIG. 6 shows in detail a heating current supply circuit for each segment of the first embodiment;

FIG. 9 is a block diagram of an endoscope to which is applied a third embodiment of the shape memory apparatus according to the present invention;

FIG. 20 is a detailed block diagram illustrating the eleventh embodiment;

FIG. 21 shows characteristics of a conventional shape memory alloy;

FIG. 22 shows characteristics of the shape memory alloy of the embodiment shown in FIG. 20;

FIGS. 26A and 26B show waveforms of heating current pulses for cooling of the twelfth embodiment obtained at high temperature;

FIG. 27 is a schematic view showing a thirteenth embodiment of the shape memory apparatus according to the present invention;

FIG. 28 is a schematic view showing a fourteenth embodiment of the shape memory apparatus according to the present invention;

FIG. 29 is a block diagram of an endoscope to which is applied a fifteenth embodiment of the shape memory apparatus according to the present invention;

FIG. 30 is a sectional view showing a configuration of an insertion section of the fifteenth embodiment;

FIGS. 31 to 34 show characteristic curves for illustrating the operation of the fifteenth embodiment;

FIG. 35 is a block diagram of an endoscope to which is applied a sixteenth embodiment of the shape memory apparatus according to the present invention;

FIG. 38 shows waveforms of heating current pulses of distal-side segments of the sixteenth embodiment;

FIG. 39 shows a bent state of the segment supplied with the heating current pulses of FIG. 38;

FIG. 40 shows waveforms of heating current pulses of proximal-side segments of the sixteenth embodiment;

FIG. 41 shows a bent state of the segment supplied with the heating current pulses of FIG. 40;

FIG. 42 shows waveforms of heating current pulses of distal-side segments according to a first modification of the sixteenth embodiment;

FIG. 43 shows waveforms of heating current pulses of proximal-side segments according to the first modification of the sixteenth embodiment;

FIG. 44 shows waveforms of heating current pulses of distal-side segments according to a second modification of the sixteenth embodiment;

FIG. 45 shows waveforms of heating current pulses of proximal-side segments according to the second modification of the sixteenth embodiment;

FIG. 46 shows waveforms of heating current pulses of distal-side segments according to a third modification of the sixteenth embodiment;

FIG. 47 shows waveforms of heating current pulses of proximal-side segments according to the third modification of the sixteenth embodiment;

FIG. 59 shows a configuration of a seventeenth embodiment of the shape memory apparatus according to the present invention;

FIG. 60 is a sectional view taken along line a—a' of FIG. 59;

FIG. 61 is a sectional view taken along line b—b' of FIG. 59;

FIGS. 66 to 70 illustrate ways a shape memory alloy of the seventeenth embodiment is connected a flange;

FIG. 71 shows a dynamic model of the SMA segment having no intermediate flange;

FIG. 72 shows a dynamic model of the SMA segment having intermediate flanges;

FIG. 73 shows a shape memory alloy of an eighteenth embodiment of the shape memory apparatus according to the present invention;

FIG. 74 shows a shape memory alloy according to a first modification of the eighteenth embodiment;

FIG. 75 shows a shape memory alloy according to a second modification of the eighteenth embodiment; and FIG. 76 shows a shape memory alloy according to a third modification of the eighteenth embodiment.

DETAILED DESCRIPTION OF THE PREFERRED EMBODIMENTS

Figure 2:
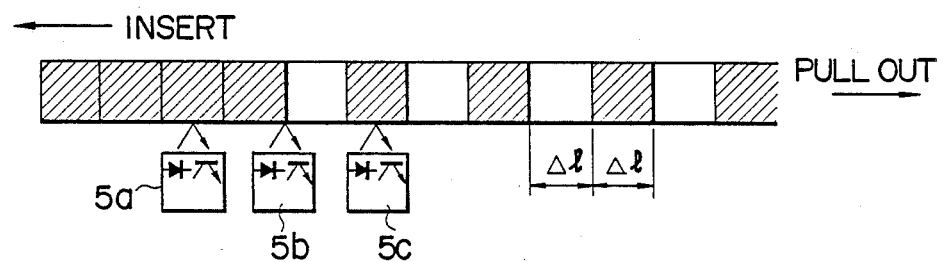
FIG. 2 is a schematic view showing an insertion distance sensor of the first embodiment.

Preferred embodiments of a shape memory apparatus according to the present invention will now be described with reference to the accompanying drawings. In the apparatus of the invention, an insertion section of an endoscope, which must be bent when it is to be inserted into the alimentary canal, is formed using an SMA. FIG. 1 is a block diagram of a first embodiment. The distal portion of insertion section 1 is divided into a plurality of segments 3a to 3e (five in number in this case). Each segment has an SMA, and is bent as the SMA recovers its memorized shape. Insertion section 1 may be inserted manually or mechanically by means of a motor (not shown) or the like.

FIG. 5 schematically shows the internal structure of one of the segments. For simplicity of illustration, the segment is supposed to be able to bend only in two directions, that is, only vertically or horizontally, and a pair of spiral SMAs 15a and 15b are arranged symmetrically along and with respect to the axis of the segment. The both ends of each SMA is fixed individually to a pair of flanges 16a and 16b. If the bending directions are four in number, including both vertical and horizontal directions, it is necessary only that two pairs of SMAs be arranged at angular intervals of 90° around the axis. Bias spring 17 is disposed on the central axis of the segment so that its both ends are also fixed individually to flanges 16a and 16b. Spring 17, which is bendable, is normally straight in shape, and serves to keep the shape of the segment straight when the SMAs are not heated. The spiral SMA memorizes its close-winding state, and are stretched into a loose-winding state when they are fixed between the flanges. Thus, when one of the shape memory elements is restored to its memorized shape, the segment bends to the side of that element. Each of SMAs 15a and 15b may be formed of a plurality of SMA coils or a single SMA coil which is turned back so as to look like a plurality of coils. If the segment must be bent only in one direction, moreover, each SMA may be linear or planar in shape with memorizing the bent shape.

Returning to FIG. 1, there is shown marking portion 4 which, formed of striped patterns each having a predetermined width ($\Delta l$), is printed on a sheathing of insertion section 1, whereby the distance of insertion of the insertion section is detected. Sensor portion 5 for detecting the striped patterns of marking portion 4 is attached to a mouthpiece, which is held at that part of a patient's body through which the endoscope is inserted into the alimentary canal, e.g., the patient's mouth. The length of the segment is 2n (n: positive integer) times as great as $\Delta l$.

Figure 3A:
FIGS. 3A to 3E show output waveforms of the insertion distance sensor during insertion.
Figure 3B:
Figure 3C:
Figure 3D:
Figure 3E:
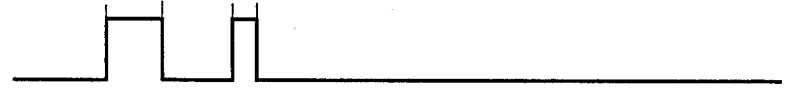
Figure 4A:
FIGS. 4A to 4E show output waveforms of the insertion distance sensor during removal of the endoscope from the body cavity.
Figure 4B:
Figure 4C:
Figure 4D:
Figure 4E:

As shown in FIG. 2, sensor portion 5 includes three photosensors 5a, 5b and 5c which, each composed of a light emitting element and a light receiving element, are arranged at intervals of $1.5 \times \Delta l$. The respective outputs of these photosensors are deviated in-phase at 90° from one another, as shown in FIGS. 3A to 3C or FIGS. 4A to 4C. FIGS. 3A to 3E show waveforms obtained when insertion section 1 is inserted into the alimentary canal, in which the waveforms of FIGS. 3A, 3B and 3C represent the outputs of photosensors 5a, 5b and 5c, respectively. Distance calculator circuit 6 obtains the insertion distance by up-counting pulses produced in response to the trailing edges of the output signal of photosensor 5a, as shown in FIG. 3D. FIG. 3E shows reset pulses used to reset a counter of circuit 6. FIGS. 4A to 4E show waveforms obtained when the endoscope is drawn out of the alimentary canal, in which FIGS. 4A, 4B and 4C represent the outputs of photosensors 5a, 5b and 5c, respectively. Distance calculator circuit 6 obtains the insertion distance by down-counting pulses produced in response to the leading edges of the output signal of photosensor 5a, as shown in FIG. 4D. FIG. 4E shows reset pulses used to reset a counter of circuit 6. A leading striped pattern, having a width of, e.g., $4 \times \Delta l$, is wider than the other patterns. When the leading pattern is detected by combining the outputs of photosensors 5a, 5b and 5c, a reset pulse indicative of a reference position is delivered.

The moving direction of marking portion 4, that is, the moving direction (for insertion or removal) of the insertion section, can be identified by delay or lead of the output phases of photosensors 5a, 5b and 5c. Also, the displacement can be determined by counting the striped patterns. The resolution of the displacement detection is $2 \times \Delta l$, twice the width ($\Delta l$) of each striped pattern.

Returning again to FIG. 1, there is shown heating current supply unit 14 which includes drivers 12a to 12e and pulse-width modulation (PWM) circuits 13a to 13e. The respective bend angles (also indicative of the direction) of first to fifth segments 3a to 3e are controlled by means of unit 14. Current supply unit 14 energizes and heats the respective SMAs of segments 3a to 3e so that the bend angles of the segments agrees with their corresponding target angles. Target bend angle $\theta 1r$ of a leading segment or first segment 3a is inputted through input unit 7. An operator inputs target value $\theta 1r$ while observing an optical image obtained by means of an optical system (not shown) for observation. Alternatively, a solid-state image sensing device, such as a CCD, may be disposed inside the distal end of the insertion section so that an image of the interior of the alimentary canal is picked up by means of the sensing device, and is indicated on an external display unit. Target values $\theta 2r$ to $\theta 5r$ of second to fifth segments 3b to 3e are outputted through memory unit 8.

Resistance detector unit 11 is connected to the SMA of each segment by means of exclusive conductor wires for resistance detection, without the aid of conductor wires connecting current supply unit 14 and the SMA. Detector unit 11 is formed of a bridge circuit having the SMA as one side thereof. Thus, it can accurately detect the resistance of the SMA without being influenced by the change of resistance of the conductor wires attributable to conduct the heating current. The output of resistance detector unit 11 is converted into bend angles $\theta 1m$ to $\theta 5m$ by means of angle calculator unit 10. Detected bend angles $\theta 1m$ to $\theta 4m$ of first to fourth segments 3a to 3d are input to memory unit 8. In response to a shift signal mentioned later, the memory unit 8 sets and delivers bend angles $\theta 1m$ to $\theta 4m$ as target values $\theta 2r$ to $\theta 5r$ for second to fifth segments 3b to 3e.

The differences between target values $\theta 1r$ to $\theta 5r$ for the individual segments and detected bend angles $\theta 1m$ to $\theta 5m$ are supplied to PWM circuits 13a to 13e of current supply unit 14. Circuits 13a to 13e supply the respective SMAs of the segments, through drivers 12a to 12e, with heating current pulses with duty ratios corresponding to the differences. The heating current pulses continue to be supplied until the differences are reduced to zero.

FIG. 6 specifically shows heating current supply unit 14a for segment 3a shown in FIG. 5. Paired SMAs 15a and 15b are provided with PWM circuits 13a1 and 13a2, respectively, and drivers 12a1 and 12a2, respectively. Difference $e\theta$ between target value $\theta$1r and detected value $\theta$1m from angle calculator unit 10 is changed into Aer and $A(1-e\frac{1}{2})$ (A is constant) by means of amplifiers 20 and 21, respectively. Then, differences er1 anf er2 between the outputs of amplifiers 20 and 21 and the resistances of SMAs 15a and 15b detected by resistance detector units 11a1 and 11a2 are obtained, and are supplied through PWM circuits 13a1 and 13a2 and drivers 12a1 and 12a2 to SMAs 15a and 15b, respectively. Thereupon, the SMA coil to be bent contracts, while the SMA coil on the opposite side stretches, thus causing the segment to bend.

Figure 7A:
FIGS. 7A to 7D are timing charts illustrating various timings of the current supply circuit of the first embodiment.
Figure 7B:
Figure 7C:

At the time of insertion, a conduction trigger pulse is delivered from control unit 9 at regular interval, as shown in FIG. 7A. As shown in shown in FIG. 7B, the resistance is detected according to a timing pulse generated during the off period of the trigger pulse. The output of sensor portion 5 is supplied to control unit 9 through distance calculator circuit 6. As shown in FIG. 7C, control unit 9 supplies a shift signal to memory unit 8 each time insertion section 1 is pushed in for the length of each segment ($n \times 2\Delta l$). In response to this shift signal, memory unit 8 sets and delivers detected bend angles $\theta$1m to $\theta$4m for the individual segments from angle calculator unit 10 as target values $\theta$2r to $\theta$5r of the bend angles for second to fifth segments 3b to 3e.

Thus, each time insertion section 1 is inserted for the length of each segment, the bend angle of the segment is detected, and the detected angle is set as the target value of the bend angle for the succeeding segment. Therefore, the insertion section acts good follow-up performance for those tubular members, such as the large intestine, whose channel configuration varies with the lapse of time. In other words, according to this embodiment, each segment is bent to the same degree as its preceding segment in the state before the insertion for the one-segment length, so that it can properly follow up the change of configuration of the tubular member into which the insertion section is inserted.

Figure 7D:

If the insertion speed of insertion section 1 is higher than the SMA control speed (which corresponds to the time interval which elapses from the instant that the target value of the bend angle is changed until each SMA is bent to the target value), the SMA cannot be actually controlled even though the detected bend angle is set as the target bend angle for the subsequent segment with every one-segment movement. In particular, the endoscope is not inserted at a fixed speed, but is rocked back and forth as it is inserted. Thus, if the target value $\theta$r is frequently changed, the control circuit will be subjected to hunting. In order to prevent the hunting, the up-count timing (FIG. 7C) is shifted from the down-count timing (FIG. 7D) so that hysteresis is produced in the timing at which the shift signal is supplied to memory unit 8 from control unit 9 to change the target value $\theta$r.

Figure 8:
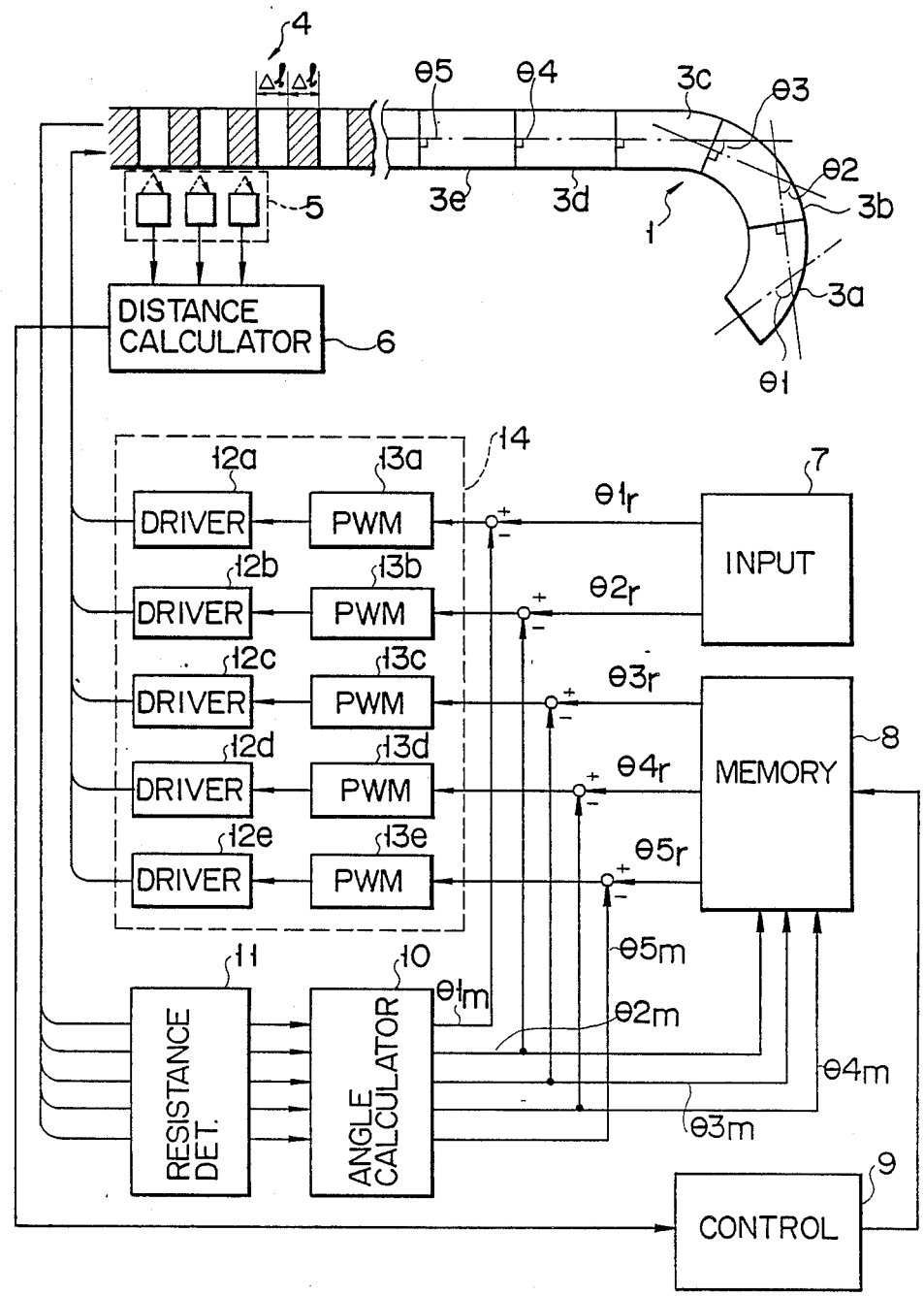
FIG. 8 is a block diagram of an endoscope to which is applied a second embodiment of the shape memory apparatus according to the present invention.

FIG. 8 shows a second embodiment of the present invention. In the first embodiment, all the segments are bent within the same plane, and the leading segment only is manually operated through input unit 7. In the second embodiment, however, a leading segment is bent within a plane perpendicular to the one within which the other segments are bent. In this case, the segment manually operated through control unit 7 is referred to as first and second segments, and bend angles $\theta$2m to $\theta$4m of second to fourth segments are set as target values $\theta$3r to $\theta$5r for third to fifth segments, respectively. In this arrangement, the insertion section can be bent in a three-dimensional manner.

FIG. 9 is a block diagram showing a third embodiment of the present invention. A pair of SMAs 15 are contained in the distal end of an endoscope, thus constituting a bending portion. Both ends of each SMA 15 are connected to driver 12 by means of conductor wires 18 for s heating current, and are also connected to resistance detector unit 11 by means of conductor wires 19 for resistance detection. Angle calculator unit 10 calculates bend angle $\theta$m on the basis of the output of resistance detector unit 11. The difference between bend angle rm and target bend angle $\theta$r from a control unit or a memory unit is supplied to driver 12 through PWM 13, whereupon driver 12 subjects SMAs 15 to pulse conduction in a corresponding manner.

In the embodiments described above, a shift signal is supplied to memory unit 8 each time insertion section 1 is pushed in for the length of each segment.

The following is a description of a fourth embodiment in which the target value is changed by supplying a shift signal to memory unit 8 with every movement for a distance snorter than each segment. If the length of each segment is $n \times 2\Delta l$, control unit 9 supplies a shift signal to memory unit 8 with every movement for half the one-segment length, i.e., $n \times D1$, thereby coping with the change of the bend angle for a displacement shorter than the one-segment length.

According to a fifth embodiment of the present invention, moreover, a first shift signal only is supplied with every movement for half the one-segment length or $n \times \Delta l$, and each subsequent one is supplied with every movement for one-segment length or $n \times 2\Delta l$. By doing this, the movement of the second segment and its successors, following the first segment, is improved in follow-up performance. In this case, the first segment is bent before insertion section 1 starts to move, so that the second segment and the subsequent ones can follow up better if they are bent faster.

In the embodiments described above, the shift signal is generated with every movement for a predetermined distance, and the detected value is used as the target valve for each succeeding segment. If the distance for the bending action is not too short, however, the bending action need not always be shifted to a directly succeeding segment, and may be shifted to the next one but one, two, or more, as in a sixth embodiment of the present invention. More specifically, the bend angle may be shifted in a manner such that the first and second segments always act in the same way and the third and fourth segments are bent following the action of the first and second segments. Thus, the bending operation can be performed in accordance with the application, ranging from fine bent channels to large ones.

A seventh embodiment of the present invention will now be described. SMAs are previously arranged in each segment in a manner such that the segments in odd numbers are horizontally bendable and the ones in even numbers are vertically bendable so that three-dimensional bending can be effected. If the insertion section is moved for a distance corresponding two segments, a shift signal is supplied. Thus, by shifting the bend angle for every other segment, horizontal and vertical bending actions can be shifted separately.

According to the above embodiments, as described above, the bend angle of each segment is detected each time insertion section 1 is moved for the predetermined distance, and the curvature of each segment is controlled using the detected bend angle as a target value for the bending control of a succeeding segment. As insertion section 1 is inserted, therefore, each segment bends to the same degree as its preceding segment, thereby properly following up the change of configuration of the insertion path. Thus, there may be provided an endoscope which can be safely and easily inserted into the alimentary canal, such as the large intestine, whose channel configuration varies with the insertion.

Figure 10:
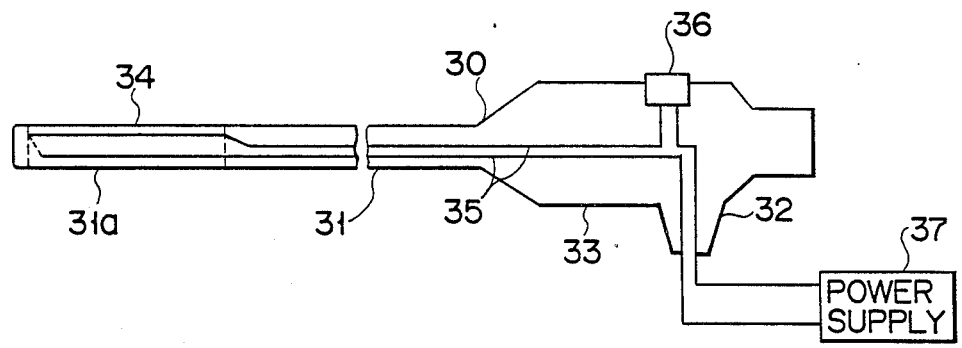
FIG. 10 is a block diagram of an endoscope to which is applied an eighth embodiment of the shape memory apparatus according to the present invention.
Figure 11:
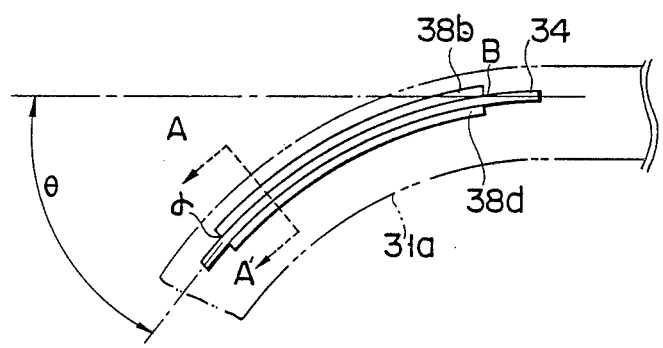
FIG. 11 is a side sectional view of a bending portion of the eighth embodiment.
Figure 12:
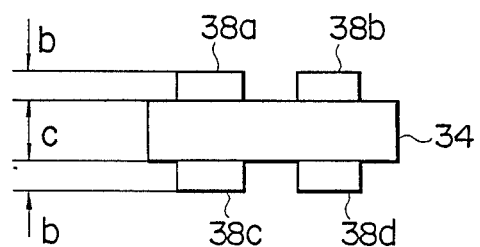
FIG. 12 is a sectional view corresponding to FIG. 11.
Figure 13:
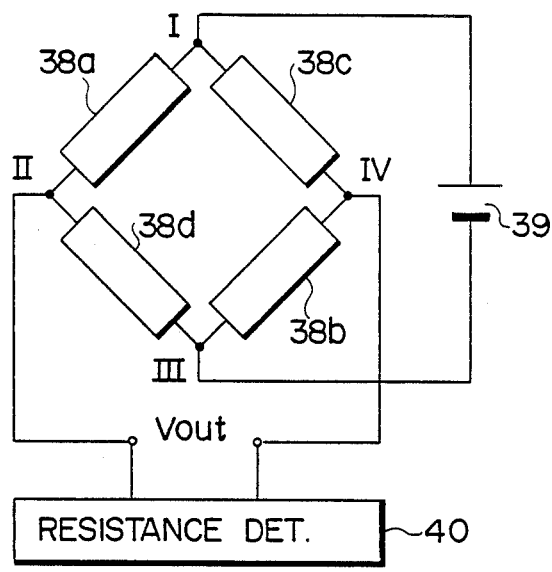
FIG. 13 is a circuit diagram of a bend angle detector circuit of the eighth embodiment.

Although the bend angle of each segment, in the embodiments described above, is detected on the basis of resistance, it may alternatively be detected directly by means of a sensor which may be attached to the SMA. The following is a description of an eighth embodiment of the present invention which is provided with the angle sensor. FIG. 10 is a schematic view showing an outline of the eighth embodiment. In endoscope 30, insertion section 31, having bending portion 31a at the distal portion thereof, and universal cord 32 are coupled to control section 33. Bending mechanism 34, composed of SMAs, is contained in bending portion 31a. In this case, each SMA is not spiral but planar in shape. The transformation temperature of SMA plate 34 is set to about 60° C., and the bent shape shown in FIG. 11, for example, is memorized into plate 34. One end of lead wires 35 for heating is connected to SMA plate 34, while the other ends of wires 35 is connected to external current supply circuit 37 through switch 36 at control section 33 By operating switch 37, SMA plate 34 can be conducted and heated to bend bending portion 31a. Four conductive rubber belts 38a to 38d are pasted on the surface of SMA plate 34, as shown in FIGS. 11 and 12, and the bend angle of bending portion 31a is detected on the basis of the change of electric resistance of the rubber belts 38a to 38d. FIG. 12 is a sectional view taken along line A—A' of FIG. 11. The rubber belts may be made of electrically conductive rubber which is formed by dispersing conductive particles or a metal filler into rubber material, more specifically, by uniformly dispersing carbon particles into silicone rubber. Conductive rubber belts 38a to 38d are pasted symmetrically on either side of SMA plate 34, and are wired in the manner shown in FIG. 13, thus forming a bridge circuit. Opposite points I and III between belts 38a and 38c and between belts 38b and 38d, respectively, are on the input side, while points II and IV between belts 38a and 38d and between belts 38b and 38c, respectively, are on the output side. The input side is connected to power source 39 by means of lead wires 35 which are inserted in insertion section 31. The output side is connected to resistance detector unit 40 in control section 33 also by means of lead wires 35. In this arrangement, a voltage between points II and IV, which varies in accordance with the bending operation, is delivered as an output, whereby the variation of the bend angle of the bending portion can be detected. Also, a display unit (not shown) for indicating the bend angle of the bending portion is connected to resistance detector unit 40.

The bending portion bends as the SMA is heated. At the same time, bend angle $\theta$ (angular variation) is detected on the basis of the change of the resistance of the conductive rubber belts. Since elongation or contraction of the rubber belts is proportional to bend angle $\theta$, the angular variation obtained is accurate.

Figure 14:
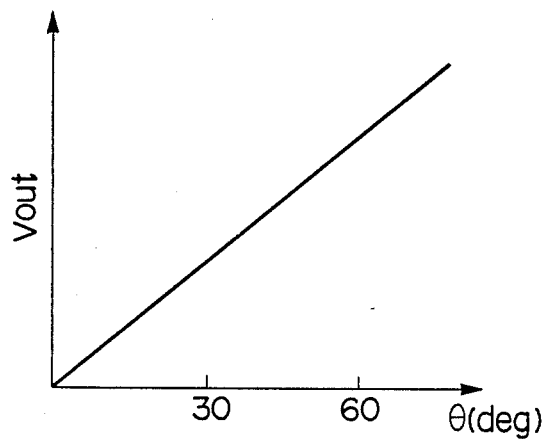
FIG. 14 shows a curve representing the relationship between the bend angle and the output of the bend angle detector circuit of the eighth embodiment.

According to an experiment, $\theta$ is proportional to voltage Vout from points II and IV, as shown in FIG. 14, so that $\theta$ can be detected by detecting voltage Vout at point II and IV. Since the conductive rubber belts must only be attached to those portions which are adapted to bend, the construction is simple.

Figure 15:
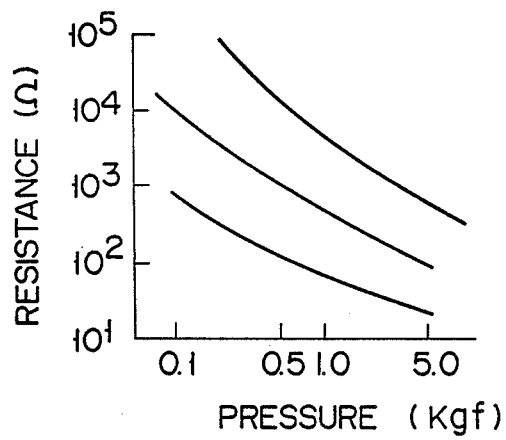
FIG. 15 shows characteristics of an angle sensor used in a ninth embodiment of present invention.

In a ninth embodiment of the present invention, four pressure-sensitive resistance elements, instead of conductive rubber belts 38a to 38d, are pasted on the surface of the SMA plate. The resistance elements are obtained by screen-printing a plastic film with pressure-sensitive conductive ink. The electric resistance of each resistance element varies as the element is pressurized. Since the resistance elements are highly flexible, they can be formed into any desired shape. FIG. 15 shows characteristics of the resistance elements. Based on these characteristics, the change of pressure acting on the elements, depending on bend angle $\theta$, can be detected as a change of resistance, thus obtaining bend angle $\theta$.

Figure 16:
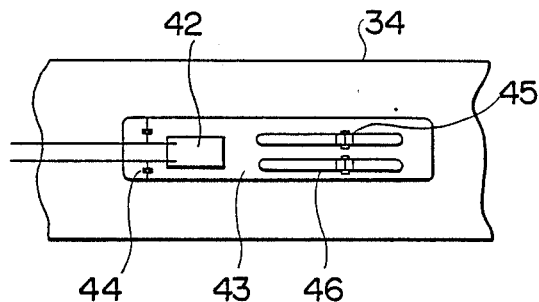
FIG. 16 shows a configuration of an angle sensor used in a tenth embodiment of the present invention.

The following is a description of a tenth embodiment of the present invention in which bend angle sensor 43, which has strain gage 42, is pasted on SMA plate 34, as shown in FIG. 16. The body of sensor 43 is formed of leaf spring on which gage 42 is pasted. One end portion of the leaf spring is fixed to plate 34 by means of fixing screws 44 penetrating holes which are bored through the one end portion. Guide groves are formed on the other end portion of the leaf spring, whereby the spring can slide even after it is attached to SMA plate 34. The other end portion of the spring is attached to plate 34 by means of fixing screws 45 which are passed through the guide grooves.

Figure 17:
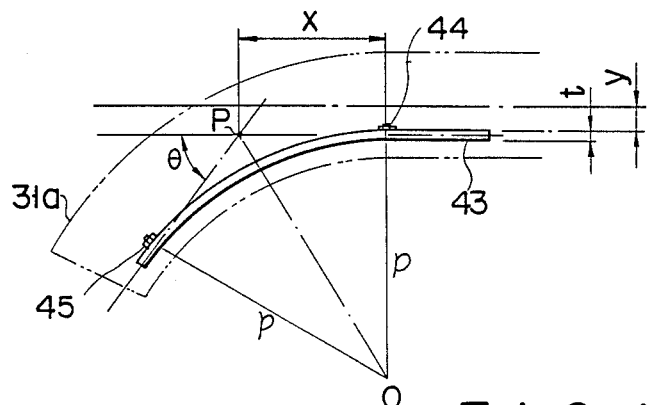
FIG. 17 is a diagram illustrating the principle of bend angle detection of the tenth embodiment.

Referring now to FIG. 17, the principle of angle detection according to this embodiment will be described. SMA plate 34 is not shown in FIG. 17. Sensor 43 is at distance $\underline{y}$ from the central axis of bending portion 31a. If the thickness of sensor 43 is $\underline{t}$, and if the horizontal distance from pivotal point $\underline{p}$ to each fixing screw 44 is $\underline{x}$, there is the following relationship between radius $\rho$ of curvature and bend angle $\theta$.

$$\rho = x \tan((180-\theta)/2). \tag{1}$$

When bending the sensing element inward (toward point O), radius $\rho 1$ of curvature is given by $$\rho 1 = x \tan((180-\theta)/2) - y. \tag{2}$$

When bending the sensing element outward, on the other hand, radius $\rho 2$ of curvature is given by $$\rho 2 = x \tan((180-\theta)/2) + y. \tag{3}$$

Also, there is the following relationship between radius $\Sigma$ and strain $\epsilon$.

$$\epsilon = t/2\rho. \tag{4}$$

From these equations, we obtain $$\theta = 180 - 2\tan-1(K/x) \tag{5}$$

where constant K is given by $K = t/(2\epsilon) + y$ for inward bending, and by $K = t/(2\epsilon) - y$ for outward bending.

Curvature strain of the leaf spring generated by the bending operation id detected as a resistance change of strain gage 42. This change of resistance is detected, and the bend angle is obtained on the basis of a previously given calibration value. Sensing elements may be provided for a plurality of joints.

Figure 18:
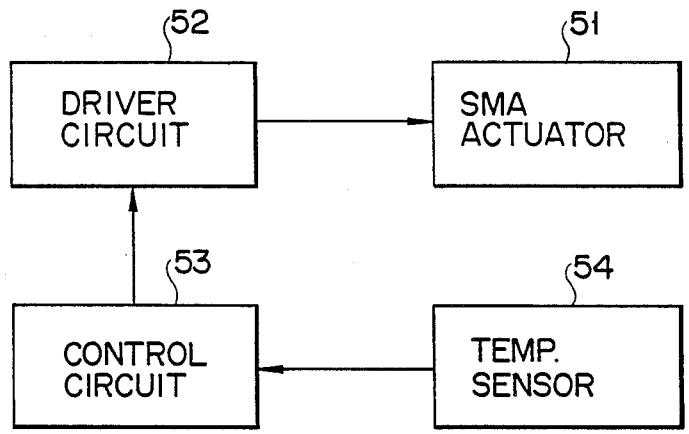
FIG. 18 is a schematic block diagram illustrating an eleventh embodiment of the shape memory apparatus according to the present invention.
Figure 19:
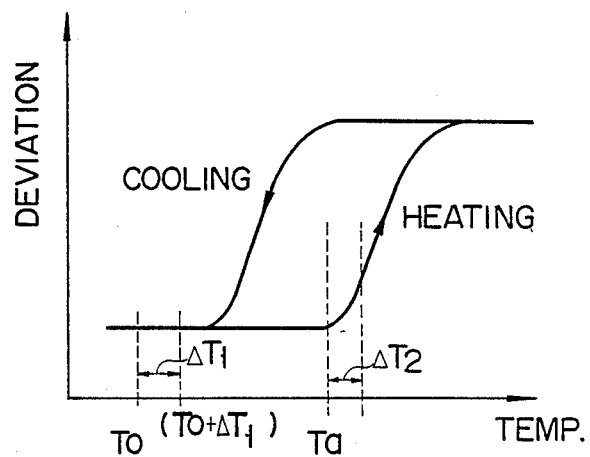
FIG. 19 shows characteristics of a shape memory alloy of the eleventh embodiment.

The following is a description of an eleventh embodiment of the present invention which relates to a driving method for a shape memory alloy whose response speed cannot be lowered by change of environmental temperature. FIG. 18 shows an outline of the arrangement of this embodiment. SMA actuator 51 having an SMA recovers irs shape to make a desired displacement, thereby driving a load, as it is conductively heated by means of driver circuit 52. When cooled, actuator 51 is restored to its original shape. Temperature sensor 54 is located beside actuator 51, whereby the working environmental temperature of actuator 51 is detected. In accordance with the detected temperature, control circuit 53 adjusts the drive amount of driver circuit 52, i.e., the amount of heating of the SMA. If the SMA is supplied with a predetermined amount of heat, its temperature attains Ta, as shown in FIG. 19. Actuator 51 is supposed to make the desired displacement at temperature Ta. At this time, however, the environmental temperature is at To. If the environmental temperature changes by $\Delta T1$ from To, the temperature of the SMA, even with the supply of the same amount of heat, cannot attain Ta, but reaches point (Ta+$\Delta T2$), i.e., the point deviating from Ta by $\Delta T2$. This indicates that the desired displacement cannot be obtained by controlling the amount of heating by means of driver circuit 52.

Accordingly, the environmental temperature is detected by means of temperature sensor 54, and control circuit 53 controls the variation of the amount of heat, compared with the predetermined amount of heat, in accordance with the difference between the detected environmental temperature and predetermined temperature To. Thus, an amount of heat such that the temperature of the SMA is accurately adjusted to Ta, without regard to the environmental temperature, can be determined, so that the desired displacement can always be obtained. According to this embodiment, moreover, control circuit 53 can increase the heating speed in accordance with the detected temperature, thereby improving the responsiveness.

FIG. 20 is a specific block diagram showing the eleventh embodiment. In order to effect accurate control without the influence of any disturbance (e.g., load), in this case, the resistance of the SMA, as well as the environmental temperature, is detected, and the difference between the detected value and the resistance corresponding to the desired displacement is also applied to control circuit 53. Resistance detector circuit 55 for detecting the resistance of the SMA is connected to SMA actuator 51. The displacement of actuator 51 is feedback-controlled on the basis of the detected resistance. Since there is a certain relationship between the resistance of the SMA and the displacement, the amount of heat from driver circuit 52 is controlled so that the detected value agrees with the resistance (target value) for the desired displacement.

An advantage of this displacement control based on the resistance is that it requires no sensor for detecting the actual displacement, thus permitting reduction of the apparatus size. According to the resistance-based control, as is generally known, hysteresis between temperature and resistance can be reduced by the use of an autagonistic type actuator. This hysteresis can be further reduced by heat treatment or some other measures. Thus, as compared with the conventional case as shown in FIG. 21, the hysteresis can be considerably reduced as indicated by the characteristic curves of FIG. 22.

The accuracy of the displacement control can be further improved by driving actuator 51 only within a range ($\Delta Tw$) such that the temperature-resistance (displacement) characteristic curves are linear.

In the arrangement of FIG. 20, the environmental temperature is detected by means of temperature sensor 54 and controlled in the same manner as in the case of FIG. 18. If temperatures of the SMA before the drive are equal to environmental temperatures To and (To−$\Delta T$), individually, there is conventionally no difference between the resistances of the SMA at the two temperatures. Accordingly, the response speed obtained with use of environmental temperature To at the time of initial drive of actuator 51 is considerably different from that obtained with environmental temperature (To−$\Delta T$). Thus, in the case where the resistance of the SMA is feedback-controlled, the responsiveness can be greatly improved by controlling the heating speed in accordance with the detected environmental temperature.

According to this embodiment, the working environmental temperature of the shape memory actuator is detected, and the amount of heating or cooling of the SMA is controlled in accordance with the detected temperature. By doing this, the accurate displacement can always be obtained, so that responsiveness of the apparatus, as well as its accuracy, can be improved.

Figure 23:
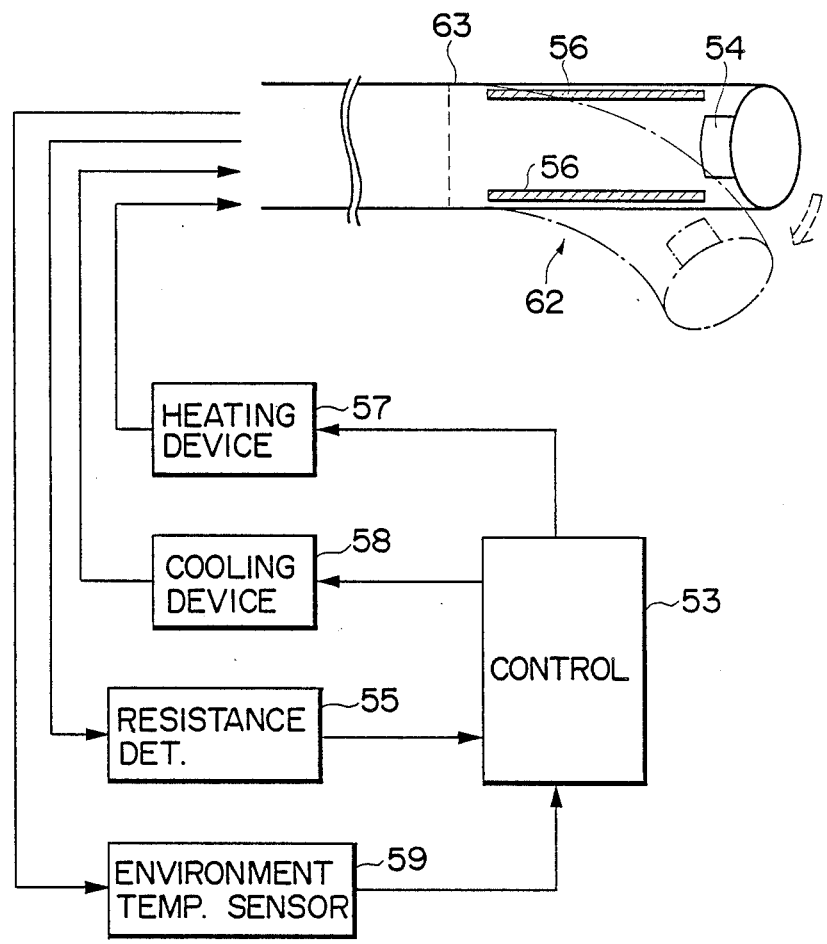
FIG. 23 is a block diagram illustrating a twelfth embodiment of the shape memory apparatus according to the present invention.

FIG. 23 is a block diagram showing a twelfth embodiment of the present invention which is applied to an endoscope. A pair of SMAs (in the form of coils or plates) 56 are vertically arranged inside bending portion 63 at the distal end portion of endoscope 62. The individual SMAs are bent in the vertical direction of FIG. 23 as they are heated. They are connected with heating device 57, cooling device 58, and resistance detector circuit 55. Temperature sensor 54 is disposed near the distal end of bending portion 63. The output of sensor 54 is supplied to environmental temperature sensor circuit 59. The respective outputs of circuits 55 and 59 are supplied to control circuit 53, which controls heating device 57 and cooling device 58.

Figure 24A:
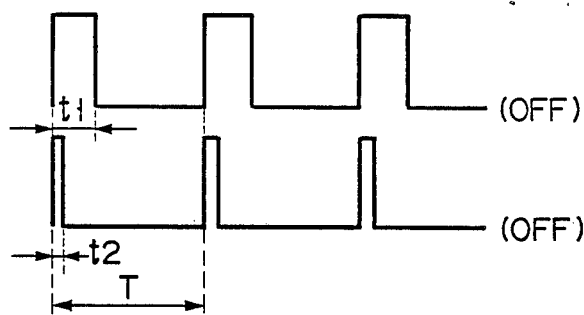
FIGS. 24A and 24B show waveforms of heating current pulses of the twelfth embodiment obtained at suitable temperature.
Figure 24B:

SMAs 56 are conductively heated by means of control circuit 53 and heating device 57. Conduction is caused pulsatively, and bending portion 63 is bent upward as current pulses with duty ratios of d1=t1/T and d2=t2/T, as shown in FIGS. 24A and 24B, are supplied to the upper and lower SMAs. The maximum duty ratio is restricted to 0.33 to prevent overheating.

During the off period of the current pulses, the resistances of SMAs 56 are measured by means of resistance detector circuit 55, and the measured values are delivered to control circuit 53.

Cooling device 58 is provided for better restoration from the memorized shape to the original shape, since natural radiation of heat cannot ensure good responsiveness. The cooling device sends cool air through an air channel (not shown), thereby cooling SMAs 56.

Figure 25A:
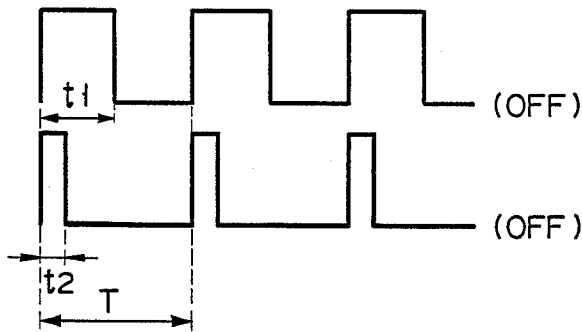
FIGS. 25A and 25B show waveforms of the heating current pulses of the twelfth embodiment obtained at a low temperature.
Figure 25B:
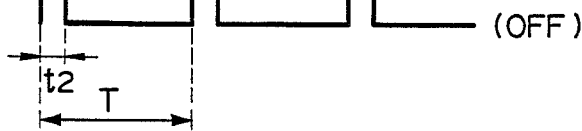

As described in connection with the eleventh embodiment, the responsiveness of the bending action of SMAs 56 may possibly be lowered by the environmental temperature, so that the environmental temperature is measured by means of temperature sensor 54. The measured environmental temperature is applied to control circuit 53, which controls the amount of current supply (duty ratio) or changes the amount of cooling in with the environmental temperature. If the environmental temperature is lower than the lower limit of working range ΔTw of FIG. 22, the duty ratio of the heating current pulses is increased, as shown in FIGS. 25A and 25B, thereby improving the responsiveness, in heating upper and lower SMAs 56 to obtain the same bend angle as in the case of FIGS. 24A and 24B. If the environmental temperature is higher than the upper limit of working range ΔTw, on the other hand, the duty ratio of the current pulses is reduced to zero, as shown in FIGS. 26A and 26B, to cool SMAs 56, and the cooling only is performed without heating. It is to be understood that the responsiveness can be improved also by changing the quantity of cool air from cooling device 58.

FIG. 27 shows a thirteenth embodiment of the present invention, in which temperature sensor 54 is attached to the distal end of forceps 61 which is passed through channel 60 of endoscope 62. The environmental temperature is measured by means of sensor 54 to control the displacement of SMAs 56. According to this embodiment, the environmental temperature is measured and controlled only at the time of initial drive, thereby improving the responsiveness. After the temperature of SMAs 56 enters working range ΔTw of FIG. 22, forceps 61, with temperature sensor 61 thereon, is removed from channel 60, thus allowing the inside of the channel to be utilized for some other purposes.

FIG. 28 shows a fourteenth embodiment of the present invention, in which heater 70 is contained in the distal end portion of endoscope 62, and the environmental temperature of SMAs 56 is always set within working range ΔTw of FIG. 22. The responsiveness can be also improved by this arrangement.

In the eleventh to fourteenth embodiments, the conductive heating is used as the heating method. It may, however, be replaced with a direct heating method utilizing heat from heaters, etc. Moreover, the cooling method is not limited to the use of cool air, and may utilize a coolant or the like.

FIG. 29 shows a general arrangement of a fifteenth embodiment of the present invention, in which endoscope 81 comprises control section 82 and insertion section 83. A plurality of series-connected segments 78a to 78g (seven in number in this case) which are bendable in two directions. Distal end piece 84 is attached to the extreme distal end of insertion section 83. The proximal end portion of section 83 is composed of flexible tube 85. Like a conventional endoscope, the endoscope of this embodiment is provided with optical systems (not shown) for observation and illumination inside insertion section 83.

Segments 78a to 78g, having equal lengths, are constructed in the same manner, as shown in FIG. 30. Flanges 87 are arranged inside sheathing 86 of insertion section 83, whereby segments 78a to 78g are connected to and divided from one another. Bias spring 88 is disposed between each two adjacent flanges 87. It is located on the central axis of section 83, and its opposite ends are coupled to their corresponding flanges 87 in front and in rear. The distal end of spring 88 at the extreme distal end of insertion section 83 is attached to distal end piece 84. Bias springs 88 keep segments 78a to 78g straight by means of their tensile force, and are adapted to bend when they are subjected to a force. Springs 88 may be formed of conventional spring wire material, e.g., spring stainless-steel wire.

In this embodiment, bias springs 88 are not uniform in bendability, and their elasticity is improved and hardness is reduced with distance from distal end piece 84. Thus, the flexibility of segments 78a to 78g of insertion section 83 increases with distance from the distal end side. More specifically, springs 88 are reduced in wire diameter with distance from the distal end side, in order to vary the degrees of elasticity and hardness of the springs. Alternatively, the effective diameter and the number of turns of the springs may be increased or combined variously for the same purpose. Alternatively, moreover, various materials may be used for bias springs 88 so that the springs on the proximal end side are higher in modulus of elasticity. Table 1 shows relative variations of these characteristics.

TABLE 1

| Segment | Distal end | Proximal end |
| --- | --- | --- |
| Spring wire diameter | Greater | Smaller |
| Effective spring diameter | Smaller | Greater |
| Number of turns | Smaller | Greater |
| Modulus of elasticity | Lower | Higher |

FIG. 30 shows a case in which bias springs 88 are reduced in wire diameter with distance from the distal end side.

Each of segments 78a to 78g is provided with two SMA coils 91a and 91b, for use as bending drive members, arranged along the axis of insertion section 83. In each segment, coils 91a and 91b, which are vertically arranged in eccentric relation, are stretched between their corresponding pair of adjacent flanges 87. The SMA as the material for SMA coils 91a and 91b may be an Ni-Ti-based alloy or Cu-Zn-Al-based alloy. The memorized shape of these coils is of a close-winding type, for example. In setting each SMA coil in its corresponding segment, it is fixed, at both ends thereof, to flanges 87 or the like in a manner such that it is stretched and distorted. The transformation temperature (austenite transformation temperature Af) of the SMA coil is previously set at 40° to 60° C.

One ends of SMA coils 91a and 91b of each segment are connected in common to grounding lead wire 90 for each segment. The other end of upper SMA coil 91a of each segment is connected to each corresponding conduction lead wire 92, and the other end of lower SMA coil 91b is also connected to each corresponding conduction lead wire 93. Lead wires 90, 92 and 93 are connected to current supply unit 96 in external light source unit 95 through the inside of insertion section 83, control section 82, and universal cord 94. Resistance detector unit 97 is also provided in light source unit 95. Detector unit 97 detects the change of resistance attributable to phase transformation of SMA coils 91a and 91b through the medium of lead wires 90, 92 and 93, thereby detecting the displacements of coils 91a and 91b, i.e., the bend angles of segments 78a to 78g, and feeds back the detected values to conduction control unit 98. In response to the detected bend angles, control unit 98 gives current supply unit 96 a current supply command such that the bend angles of segments 78a to 78g agree with desired angles. The current supply system used is the pulse-width modulation (PWM) system in which the conduction time is varied in accordance with the current supply command. Thus, the resistances of SMA coils 91a and 91b are detected during a quiescent period between conduction periods.

The following is a description of the operation of the fifteenth embodiment. SMA coils 91a or 91b are supplied with current from current supply unit 96 through lead wires 92 or 93. Thereupon, energized coils 91a or 91b is heated by means of their own electric resistances to the transformation temperature. As a result, the heated SMA coils are displaced so as to be restored to the memorized close-winding state. Thus, segments 78a to 78g are bent toward energized coils 91a or 91b. The current must be supplied only to SMA coils 91a or 91b of those segments which are to be bent. By controlling the amount of current supply while detecting the resistances of SMA coils 91a and 91b, control for predetermined bend angles can be effected to obtain a desired bent shape.

In the case of the bending operation described above, if bias springs 88 of segments 78a to 78g have the same bending characteristic, the driving forces needed to bend the segments without springs 88 are greater with distance from the distal end side, as mentioned before. Thus, in bending the segments on the proximal end side, they must be moved sustaining the weight of those segments which are connected on the distal end side by means of themselves. In bending the segments on the distal end side, on the other hand, the load is reduced, so that the necessary bending forces become smaller. FIG. 31 illustrates this situation. Even though bending drive members 91a and 91b of segments 78a to 78g are equally energized to be subjected to equal bending forces, therefore, the bend angles of the segments are narrowed with distance from the distal end side. FIG. 32 illustrates this situation. This effect constitutes a hindrance to the feedback control of resistance for the attainment of fixed bend angles with use of a fixed amount of current supply.

According to the fifteenth embodiment, in contrast with this, the elasticity of bias springs 88 of segments 78a to 78g is improved with distance from distal end piece 84 of insertion section 83, so that the forces needed to bend the segments become smaller with distance from the distal end side. Although the bending forces for the segments without springs 88 are greater on the proximal end side, therefore, the comprehensive bending force for the segments, including the bending forces of springs 88, is uniform throughout the length of insertion section 83. FIG. 33 illustrates this situation.

Accordingly, if bending drive members 91a and 91b of segments 78a to 78g are equally energized, the segments are bent to the same bend angle, depending on the amount of current supply, as shown in FIG. 34. This effect is suited for the control system in which the resistance is feedback-controlled to obtain the fixed bend angles with use of the fixed amount of current supply.

Thus, according to the fifteenth embodiment, the bendability of the segments is made higher with distance from the distal end side, so that the bend angles of the segments can be equalized, for easier bending control, by equally controlling the bending drive members of the segments.

The forces needed to bend the segments may be equalized by making the wall of the sheathing for the segments thinner with distance from the distal end side, instead of varying the bending characteristic of the bias springs. When using a flex or a braid as a member constituting the sheathing, for example, it is necessary only that the hardness of the flex or braid be made smaller with distance from the distal end side. More specifically, the wall thickness of the flex or the wire diameter of the braid may be reduced with distance from the distal end side. When circulating air to cool the conductively heated bending drive members, the amount of air supply may be increased with distance from the proximal end side so that the drive members of the distal end side are cooled more. Thus, the temperature is restrained from rising during regular current supply so that the bending forces of the segments on the distal end side are smaller.

FIG. 35 shows a general arrangement of a sixteenth embodiment of the present invention, in which marking portion 101, formed of striped patterns each having a predetermined width $\Delta$, is provided on sheathing 86 of insertion section 83, whereby the distance of insertion of the insertion section is detected. Three photosensors 99, each including a light emitting element and a light sensing element, are arranged at regular intervals of $1.5\Delta$ in the direction of insertion. The photosensors, which are attached to a mouthpiece, are used to detect marking portion 101. The outputs of photosensors 99 are supplied to control unit 98 through insertion distance detector unit 100. Detector unit 100 detects the insertion direction on the basis of delay or advance of the phase of the output pulses from three photosensors 99, and determines the amount of movement (insertion distance) by the number of output pulses.

Figure 36:
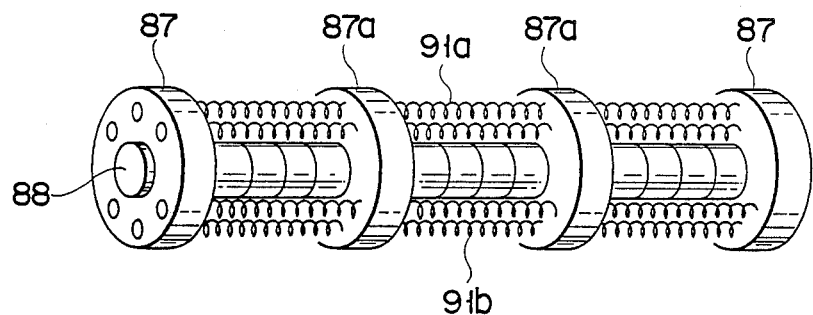
FIG. 36 shows a configuration of one SMA segment of the sixteenth embodiment.

FIG. 36 shows an arrangement of one of the segments according to the sixteenth embodiment. In this arrangement, intermediate flanges 87a are disposed between end flanges 87, and each of upper and lower SMA coils 91a and 91b in the segment is threefold. All the segments have the same bending characteristic.

Figure 37:
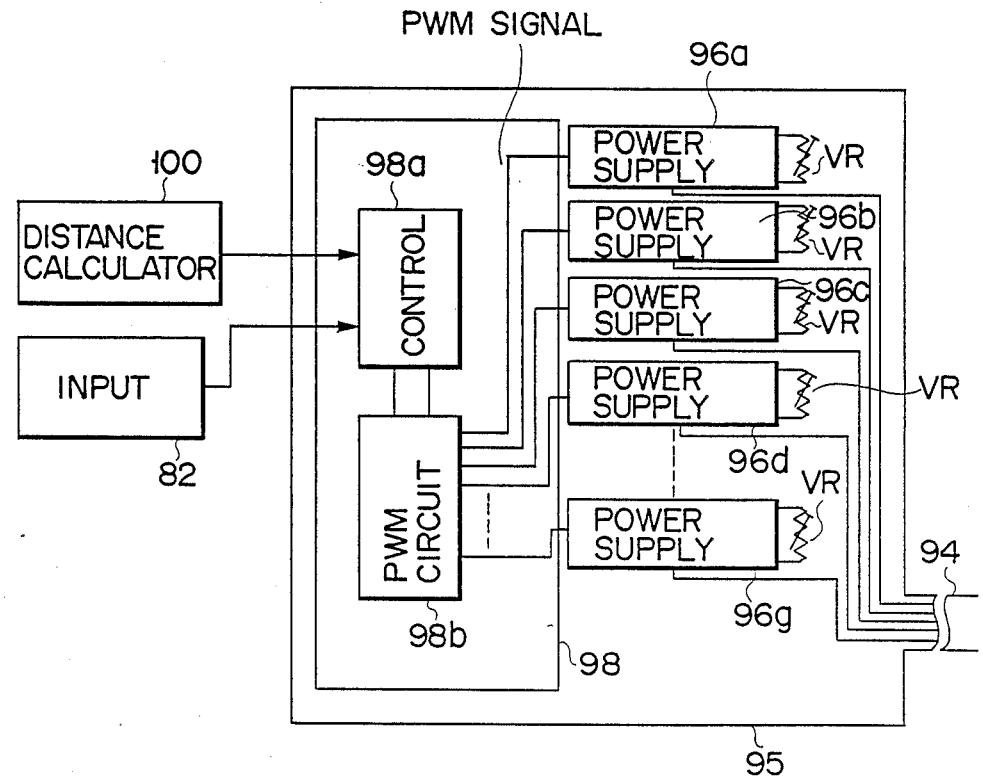
FIG. 37 is a circuit diagram of a heating current supply circuit of the sixteenth embodiment.

FIG. 37 shows details of control unit 98 of the sixteenth embodiment. Operation control portion 98a is supplied with an insertion distance signal for insertion section 83 detected by means of insertion distance detector unit 100 and an operation signal for determining the bending direction of the distal end of insertion section 83 designated by means of control section 82. Based on these signals, control portion 98a determines a target value of the bend angle for each segment. In this case, the so-called shift control is performed in the manner described in connection with the first embodiment. At the time of insertion, the target value of the bend angle, including the bending direction of leading segment 78a, is set in accordance with the operation signal. When insertion section 83 is pushed in for the one-segment distance, the bend angle of each segment is set as the target value of the bend angle for each subsequent segment. In response to the target bend angle, PWM control circuit 98b generates a PWM signal, and supplies it to heating current supply circuits 96a to 96g of each segment. Output pulse voltages from circuits 96a to 96g can be variably adjusted by means of variable resistor VR.

The following is a description of the operation of the sixteenth embodiment. As mentioned before, the segments on the proximal end side are subjected to greater loads than the ones on the distal end side. Since the segments have the same bending characteristic, however, the same bend angle cannot be obtained by uniform PWM control. Thereupon, according to the sixteenth embodiment, the amount of current supply to the individual segments is varied with respect the same target bend angle. More specifically, the voltage of the PWM signal and, therefore, the amount of current supply are increased with distance from the distal end side. FIG. 38 shows current pulse waveforms obtained when the segments on the distal end side are bent, while FIG. 39 shows the behavior of insertion section 83 in this state. FIG. 40 shows current pulse conduction waveforms obtained when the segments on the proximal end side are bent, while FIG. 41 shows the behavior of section 83 in this state. Symbols A and B indicative of the axis of ordinate of FIGS. 38 and 40 correspond to bending directions A and B of FIGS. 39 and 41, respectively. As seen from FIGS. 38 and 40, amplitudes V1' and V2' of PWM voltages on the proximal end side are larger than amplitudes V1 and V2 on the distal end side, so that the amount of current supply is greater on the former side. The voltage amplitudes are adjusted by means of variable resistors VR which are connected individually to current supply circuits 96a to 96g. The voltage amplitude for each segment may be set in accordance with the bending force of each segment without the bias spring, as shown in FIG. 31. Thus, equal bend angles can be easily obtained by varying the applied voltage depending on the position of the segment, without neglecting the uniformity of the PWM control irrespective of the segment location.

The adjustment of the current supply for each segment can be modified variously. FIG. 42 shows current waveforms for the segments on the distal end side, according to a first modification of the sixteenth embodiment, while FIG. 43 shows current waveforms for the segments on the proximal end side. In this case, pulsewidth control is used. Thus, pulse width w is small on the distal end side, and becomes greater with distance therefrom; the pulse width is greater on the proximal end side where the load, such as the weight of the segments themselves, is greater. The bend angle is controlled by changing the pulse amplitude.

FIG. 44 shows current waveforms for the segments on the distal end side, according to a second modification of the sixteenth embodiment, while FIG. 45 shows current waveforms for the segments on the proximal end side. In this case, bias voltage VB is continually applied to current pulses during the PWM control. Bias voltage VB' for the segments on the proximal side is set to be higher than that on the distal side. The amount of current supply on the proximal end side can be made greater also by doing this.

FIG. 46 shows current waveforms for the segments on the distal end side, according to a third modification of the sixteenth embodiment, while FIG. 47 shows current waveforms for the segments on the proximal end side. In conductively heating the shape memory alloy, as is conventionally known, the amount of current supply is temporarily increased in the initial stage of heating, in order to improve the responsiveness of the shape recovery action and the heating speed. By this method, conduction time $t_0$ for initial heating of the segments is increased with distance from the distal end side. Thus, the heating speed is higher at the proximal end side, so that the amount of initial production of bending force and, therefore, the total bending force can be increased.

Figure 48:
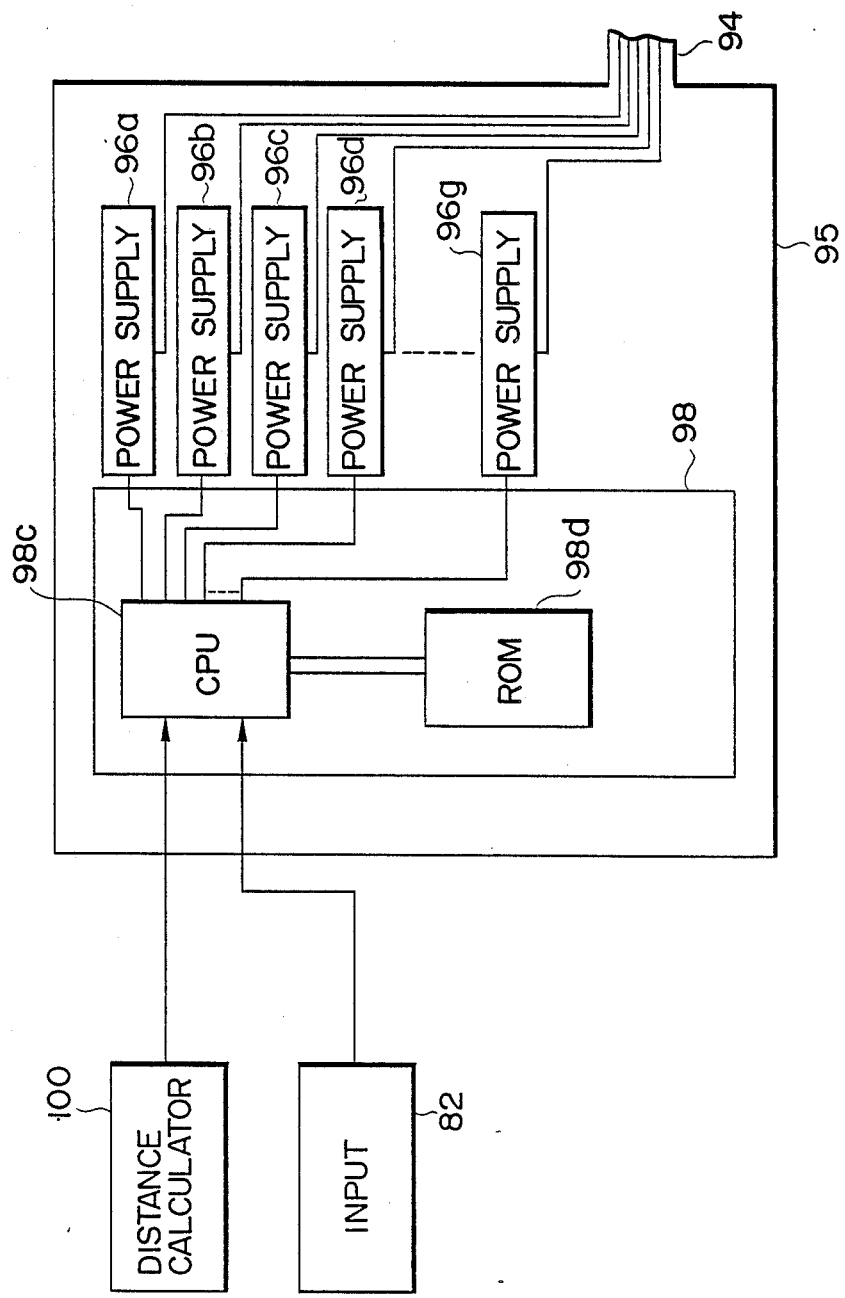
FIG. 48 is a circuit diagram of a heating current supply circuit according to a fourth modification of the sixteenth embodiment.

In the conduction control circuit of FIG. 37, a hardware circuit is used to form means for changing the amount of current supply in accordance with the location of the segments. Alternatively, however, the amount of current supply may be changed by means of software, as shown in FIG. 48. More specifically, conduction control circuit 98 may be composed of CPU 98c and waveform pattern recording ROM 98d so that the change of the amount of current supply for each segment is previously stored in ROM 98d.

Although the present invention is applied to an endoscope according to the embodiments described above, it may be also applied to apparatuses for other purposes than medical service, as well as to catheters or other medical instruments. Although the pulse conduction for heating, e.g., the PWM conduction, has been described herein, moreover, a drive method using continuous conduction is also applicable if the amount of current supply is varied for each segment. Furthermore, the bending directions of the segments are not limited to two in number, and may be increased to three or more by providing three or more bending drive members.

According to this embodiment, as described above, the bending portion can be controlled uniformly and securely.

Figure 49:
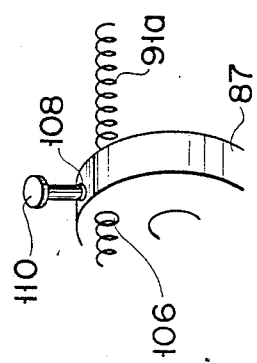
FIGS. 49 to 58 illustrate various ways a shape memory alloy fixed to a flange.

The following is a description of a specific arrangement for fixing SMA coil 91a (or SMA coil 91b; to be repeated hereinafter) to flange 87 (or intermediate flange 87a; to be repeated hereinafter) in each SMA segment of the present invention. FIG. 49 shows a first example, in which pin hole 108 is bored in flange 87 so as to extend at right angles to hole 106 through which coil 91a is passed. Retaining pin 110 is inserted into pin hole 108 in a manner such that coil 91a is passed through hole 106. Thus, pin 110 is held between two adjacent turns of SMA coil 91a, thereby fixing the coil to flange 87.

In the SMA segment constructed in this manner, the distance between end flanges 87 or between intermediate flanges 87a is lengthened or shortened, that is, changed, by simultaneously heating or cooling all SMA coils 91a and 91b. Also, bias spring 88 can be bent by selectively energizing upper or lower SMA coil 91a or 91b. When the SMA coil is transformed in this manner, it is subjected to an axial tensile force. Since the coil is fixed to end flange 87 and intermediate flange 87a by means of retaining pins 110, however, the transformation of the coil can be securely transmitted to flanges 87 and 87a. The uniform displacement can be performed by fixing the coil to the intermediate flange 87a.

Figure 50:
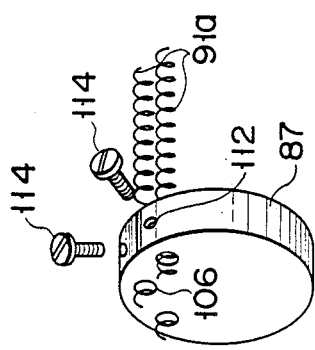

In the example shown in FIG. 50, tapped holes 112 are bored in flange 87 so as to extend at right angles to through holes 106. Retaining screws 114 are screwed individually into holes 112 so that each screw 114 is held and fixed between two adjacent turns of its corresponding SMA coil 91a.

In the fixing methods shown in FIGS. 49 and 50, the retaining means, such as pin 110 or screws 114, cannot fully close through holes 106, so that cooling air can pass through holes 106. Thus, the SMA coils can be protected against uneven temperature distribution, due to a partial rise in temperature, and from partial fatigue. As a result, the control performance for displacement and the life performance of the apparatus are improved.

Figure 51:
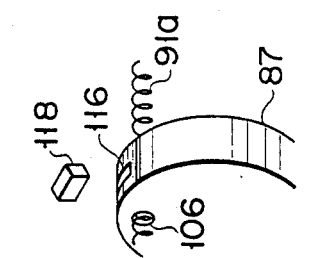

In the example shown in FIG. 51, groove 116 is formed on each flange 87 so as to extend at right angles to through hole 106. Plate 118 is fitted in groove 116 so as to be held between two adjacent turns of SMA coil 91a, thereby fixing the coil.

Figure 52:
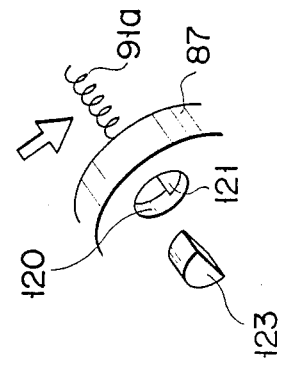

In the example shown in FIG. 52, through hole 120, having a diameter a little greater than that of SMA coil 91a, is bored through flange 87. Semicircular plate 121 for retaining coil 91a protrudes inside hole 120. It is held against coil 91a in through hole 120, in the direction of the arrow, and fixed by means of bush 123 forced into the gap inside hole 120.

Figure 53:
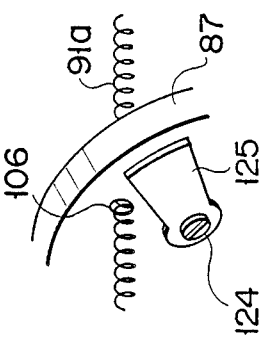

In the example shown in FIG. 53, slide plate 125, which is rockable around pivot pin 124, is disposed in the vicinity of through hole 106. After SMA coil 91a is passed through hole 106, plate 125 is rocked along flange 87 to be held between two adjacent turns of coil 91a, thereby fixing the coil.

Figure 54:
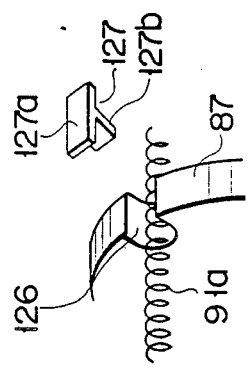

In the example shown in FIG. 54, flange 87 has notch 126 which opens to the outer peripheral edge thereof. After SMA coil 91a is fitted into notch 126 from the opening side thereof, T-shaped plate 127 is fixed to the opening of the notch. Plate 127 is formed of lid portion 127a and leg portion 127b. Lid portion 127a serves to close the opening of notch 126, and leg portion 127b is adapted to be held between two adjacent turns of coil 91a, thereby fixing the coil.

Figure 55:
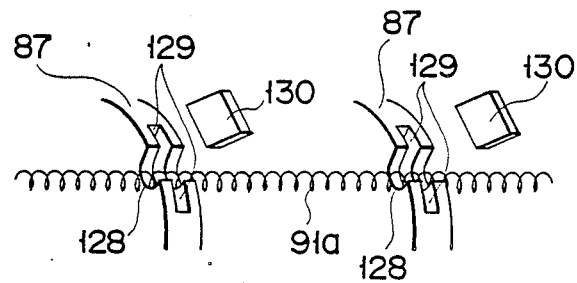

In the example shown in FIG. 55, flange 87 has notch 128 which opens to the outer peripheral edge thereof, and engaging grooves 129 are formed individually on the opposite inner side faces of notch 128. After SMA coil 91a is fitted into notch 128 from the opening side thereof, retaining plate 130 is fixed to groove 129. The lower end edge of plate 130 is adapted to be held between two adjacent turns of coil 91a, thereby fixing the coil to flange 87.

Thus, in the examples shown in FIGS. 54 and 55, the ranges of extension and contraction of SMA coils 91a may be made uniform by equalizing the number of turns of coils 91a between flanges 87, e.g., intermediate flanges 87a, at the time of assembly. In this case, T-shaped plate 127 or retaining plate 130 can be attached while observing the fixing position of SMA coil 91a through the opening of the notch. Thus, the displacement of the actuator can be made uniform.

Figures 56, 57:
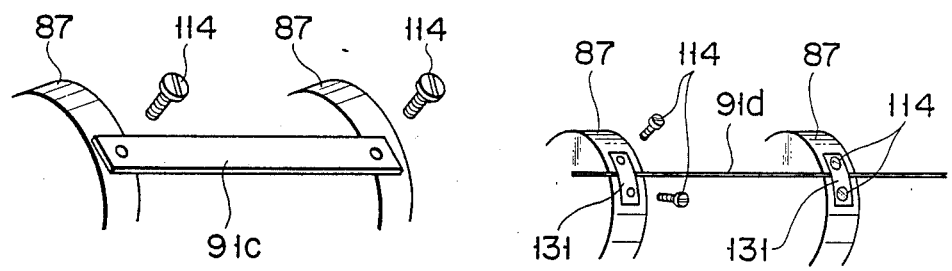

In the example shown in FIG. 56, SMA plate 91c is used in place of the SMA coil. Both end portions of plate 91c are fixed individually to the respective outer peripheral surfaces of each two adjacent flanges 87 by means of retaining screws 114.

In the example shown in FIG. 57, linear SMA wire 91d is used in place of the SMA coil. Both end portions of wire 91d are fixed individually to the respective outer peripheral surfaces of each two adjacent flanges 87 by means of fixing plates 131 and retaining screws 114.

Figure 58:
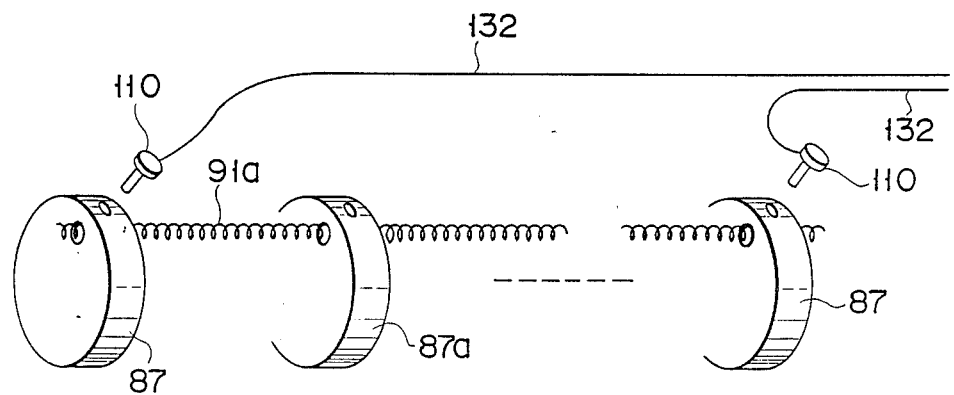

In the example shown in FIG. 58, retaining pin 110 shown in FIG. 49 is formed of an electrically conductive member, and its tip end portion is brought into contact with SMA coil 91a. Conductor wire 132 is connected to the head of pin 110 by soldering, whereby coil 91a can be energized through conductor wire 132 and pin 110. If retaining pin 110 has a temperature sensor for detecting the temperature of SMA coil 91a, the temperature of that portion of coil 91a around pin 110 can be measured. Thus, overheating can be prevented, and extension and contraction can be controlled. Retaining pin 110 of FIG. 58 may be replaced with retaining screws 114 of FIGS. 50, 56 and 57, plate 118 of FIG. 51, bush 123 of FIG. 52, slide plate 125 of FIG. 53, T-shaped plate 127 of FIG. 54, or retaining plate 130 of FIG. 55.

By thus fixing the SMA elements to the flanges by means of the retaining members, the transformation of the SMA elements can be securely transmitted to the flanges. Thus, when using the segment as an actuator, the transformation can be effected with high reliability.

Figure 62:
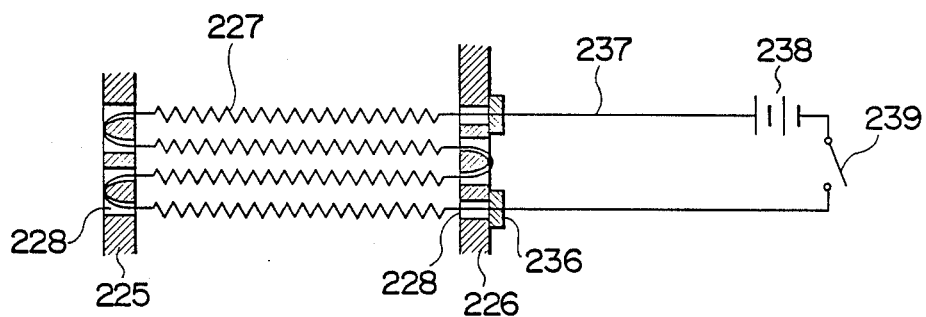
FIG. 62 is a circuit diagram of the seventeenth embodiment.

The following is a description of a seventeenth embodiment of the present invention which relates to cooling of the SMA element. FIG. 59 shows an arrangement of this embodiment. FIGS. 60 and 61 are sectional views taken along lines a-a' and b-b', respectively, of FIG. 59. Insertion section 221 of an endoscope comprises flexible tube portion 222 and bending portion 223 attached to the distal end portion thereof. Bending portion 223 includes a mechanism which is adapted to bend in two opposite directions. Flexible tube portion 222 is formed of flexible tube 224, and bending portion 223 is composed of two flanges 225 and 226 and SMA coils 227 of Ni-Ti alloy or the like which are stretched between flanges 225 and 226 so as to be vertically symmetrical but with a shearing strain of several percent. Flange 225 is provided, at the peripheral edge portion thereof, with holes 228 through which SMA coils 227 are passed and inlet port 229a through which cooling air is passed. Exhaust port 229b is formed at the peripheral edge portion of flange 226. Through hole 233 is bored through the central portion of each flange, and is penetrated by light guide fiber 230, image guide fiber 231, and air tube 232. Bias spring 235, covered by protecting tube 234, is disposed between flanges 225 and 226 so that its ends are connected individually to the flanges. As shown in FIG. 62, each SMA coil 227 is quadruplicated between flanges 225 and 226 as if it were four in number, extending through its corresponding hole 228 in two opposite directions. Each end of each coil 227 is connected to lead wire 237 by means of coupling member 236. Connectors 236 also serve to fix coils 227 to flange 226. Each lead wire 237 is connected to switch 239 through power source 238, thus constituting a closed circuit.

Bending portion 223 is covered by sheathing tube 240. The distal end portion of bending portion 223 is fitted with cover 241, and its proximal end portion is coupled to flexible tube 224. Tube 240 is formed of synthetic resin material. Fluid passage 240a is defined inside the sheathing tube. Filmy knurls 242, for use as partitioning members for dividing the four lines of SMA coil 227, protrude from the inner surface of passage 240a. Each extending in the axial direction of tube 240, the knurls are arranged circumferentially at regular intervals. Thus, the space between sheathing tube 240 and protecting tube 234 is divided into a plurality of chambers by means of knurls 242, and the individual lines of SMA coils 227 are passed through the chambers.

Cover 241 is provided with illumination window 243 and observation window 244 connected optically to light guide fiber 230 and image guide fiber 231, respectively. The distal end of air tube 232 opens into space 245 which is defined by cover 241 and flange 225. The proximal end portion of fiber 230 is connected light source 246 by means of a connector or the like. The proximal end portions of fiber 231 and tube 232 are connected to eyepiece 247 and air pump 248, respectively.

Thus, if one of switches 239 is turned on, SMA coils 227 are conductively heated to attain a transformation temperature by means of their own Joule heat, thereby generating a shape recovering force for axial contraction. Since the central axis of bending portion 223 is prevented from easily contracting by bias spring 235, bending portion 223 bends toward the heated coil. If the other switch is turned on, bending portion 223 bends in the opposite direction. After the heating, SMA coils 227 must be cooled in order to improve the responsiveness with which bending portion 223 is restored from a bent state to a straight state. Thereupon, if the cooling air is fed from air pump 248, it first enters space 245 through air tube 232, and is then discharged into fluid passage 240a between sheathing tube 240 and protecting tube 234 through inlet port 229a of flange 225. SMA coils 227 are cooled by the cooling air between knurls 242 which are formed on the inner surface of tube 240. The cooling air is fed back through exhaust port 229b of flange 226.

Axial knurls 242 of sheathing tube 240 serve to rectify the flow of cooling air in the axial direction, thereby ensuring efficient, uniform cooling of SMA coils 227. If they are formed of soft resin, knurls 242 can improve the cooling effect, without substantially spoiling the flexibility of bending portion 223.

Figure 63:
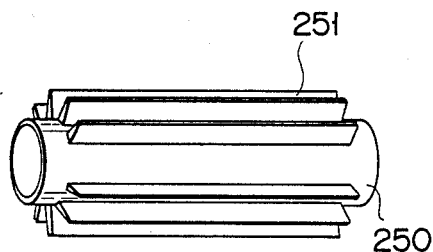
FIG. 63 shows a first modification of the seventeenth embodiment.
Figure 64:
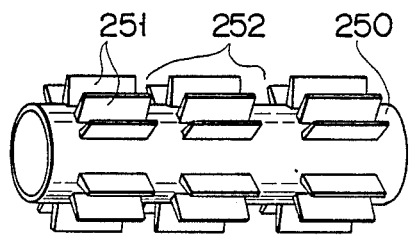
FIG. 64 shows a second modification of the seventeenth embodiment.

In this embodiment, sheathing tube 240 is provided with knurls 242. As shown in FIG. 63, however, knurls 251 may be formed on the outer peripheral surface of protecting tube 250. For higher flexibility, knurls 251 may be divided by notches 252, as shown in FIG. 64. Moreover, the fluid is not limited to air, and may alternatively be a liquid.

Figure 65:
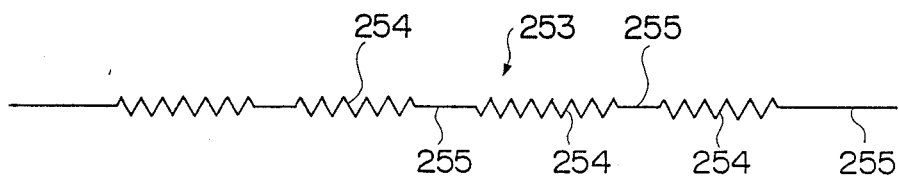
FIG. 65 shows a third modification of the seventeenth embodiment.

Each SMA coil 227, which is in the form of an integral coil, may be replaced with SMA coil 253 which is formed of coil portions 254 of the same number of turns and straight portions 255 arranged alternately, as shown in FIG. 65.

In fixing SMA coil 253 to flange 256, coil 253 never fails to be passed through hole 257 in flange 256 in a manner such that it is folded back at one of its straight portions 255 as shown in FIG. 66. Therefore, the number of turns of coil portion 254 need not be adjusted during or after the assembly work, thus permitting easier assembling. Since turn piece 258 of flange 258 has a curved surface, moreover, SMA coil 253 can be prevented from snapping.

As shown in FIG. 67, furthermore, coil portion 254 and straight portion 255 of SMA coil 253 may be connected by means of coupling members 259.

In some cases, an intermediate flange or flanges may be disposed in the middle of bending portion 223. In these case, as shown in FIGS. 68 to 70, the force of extension or contraction of each SMA coil 227 can be best transmitted to bending portion 223 in bending action by freeing coil 227 from intermediate flange 260. As described above, the coil is fixed to the intermediate flange to attain a uniform displacement.

In the arrangement shown in FIG. 68, the diameter of through hole 262 in intermediate flange 260 is greater than that of SMA coil 227, and coil 227 is passed through hole 262. Thus, coil 227 is kept free from intermediate flange 260, with respect to the direction of extension and contraction of the coil.

In the arrangement shown in FIG. 69, notch 264 is formed on the outer peripheral edge of intermediate flange 260, the intermediate portion of SMA coil 227 is fitted in notch 264, and the opening of notch 264 is covered by means of plate 266. According to this arrangement, it is unnecessary to take the trouble to insert the SMA coil into a through hole, so that the coil can be easily replaced in case of disconnection or the like.

In the arrangement shown in FIG. 70, intermediate flange 260 is located in the middle of bias spring 235, and spring 235 and flange 260 are coupled to SMA coil 227 by means of bendable coupling members 268. As coil 227 extends or contracts, member 268 stretches or bends.

If SMA coil 227 is thus freed from intermediate flange 260 with respect to its extending direction, the following effect can be produced. In this state, intermediate flange 260 is not subjected to any force, so that the shape recovering force of coil 227 acts only between end flanges 225 and 226, thus providing a dynamic model as shown in FIG. 71. If SMA coil 227 is fixed to intermediate flange 260, on the other hand, the recovering force of the coil is divided into equal parts. FIG. 72 shows a dynamic model for this case.

If the point of action of SMA coil 227 is A, and the junctions between bias spring 235 and flanges 225 and 226 are B and C, respectively, as shown in FIG. 71, deflection angle 6 of spring 235 is given by $$\theta = F \cdot AB \cdot BC / 8EI, \quad (6)$$

where E and I are the modulus of longitudinal elasticity and the second moment of area, respectively, of bias spring 235.

If the bending portion is divided into three parts by two intermediate flanges 260, as shown in FIG. 72, deflection angle $\theta'$ is given by $$\theta = F \cdot AB \cdot BC / 36EI. \quad (7)$$

Accordingly, general deflection angle 8 of bias spring 235 is $$\theta = \theta = F \cdot AB \cdot BC / 12EI. \quad (8)$$

As seen from equations (6) and (8), the deflection angle obtained when the SMA coils are fixed to the intermediate flanges is equal to 2/3 of that obtained when the coil is free. Thus, the bending angle can be made 1.5 times wider if the coils are not fixed to the intermediate flanges. Moreover, if more intermediate flanges are used, then the bending angle naturally is reduced in proportion.

The following is a description of further examples of arrangements for a higher cooling effect. In the example shown in FIG. 73, an SMA coil is constructed so that linear ground metal 272 of SMA is formed into the shape of a coil spring, and the surface of the metal is oxidized black to form black oxide film 274. Thus, the outer surface of the SMA coil is blackened, so that heat radiation is made better or faster than in the case of direct use of ground metal, and therefore, the cooling effect is higher.

In the example shown in FIG. 74, the surface of wire 276, for use as a material of an SMA coil, is formed with indentations to widen the surface area or the area of heat radiation, and is coated with dark brown paint.

Any other cooling means may be combined with the arrangements of FIGS. 73 and 74.

In the example shown in FIG. 75, heat pipe 278 is passed through the SMA coil of FIG. 73 along its axis, whereby the effect of heat radiation is improved to ensure quick, uniform cooling.

FIG. 76 shows an example in which bending drive SMA coils are arranged vertically or horizontally inside bending portion 279 of the insertion section of the endoscope, so as to extend along the axis thereof. As shown in FIGS. 73 to 75, each SMA coil 280 is constructed so that a plurality of coil portions 282, formed of a coiled SMA wire, are connected in a line by means of fixing members 284. Coil portions 282 are conductively heated to be contracted, thereby bending the bending portion to the contracted side by the agency of fixing members 284. If the current supply is cut off, coil portions 282 radiate heat, thereby returning to their original straight shape. Thus, the bending portion is restored to its original configuration.

In this case, the original straight shape cannot be recovered unless the heat radiation is satisfactory. As mentioned before, however, the surface of each SMA coil is colored or shaped for good heat radiation, so that the coil can be restored to the original straight state immediately after it is bent. The insertion section of endoscope is also provided with optical system 286 for observation and air channel 288 through cooling air is supplied. The cooling air is introduced through channel 288 into bending portion 279, thereby quickly cooling the SMA coils.

In the embodiments described above, the SMA is used to bend the insertion section of the endoscope. The present invention is not, however, limited to those embodiments, the SMA may be used to bend catheters and the like for insertion. Moreover, the displacement of the SMA may be utilized for a linear motion to drive load, instead of being utilized for the bending drive.

What is claimed is:

1. A shape memory apparatus comprising:
    a probe composed of a plurality of segments coupled to one another and adapted to be moved inside a tubular member, each said segment including a shape memory element so that the probe bends as the shape memory element changes its shape;
    means for inputting a target value of the bend angle for a specific segment;
    means for detecting the bend angle of each said segment each time the probe is moved for a predetermined distance; and
    temperature adjusting means connected to said probe, said input means, and said detecting means, said adjusting means serving to control the temperature of the shape memory element so that the detected bend angle of the shape memory element agrees with such a target angle that said inputted angle being set as the target angle for the specific segment, and said detected bend angle of each segment being set as the target angle for segment following the specific segment with respect to the moving direction.

2. The apparatus according to claim 1, in which said specific segment is the leading segment of the probe, and said detected bend angle of each said segment is set as the target angle for the next segment with respect to the moving direction.

3. The apparatus according to claim 2, in which the detected bend angle of each segment is set as said target bend angle for each succeeding segment each time the probe is moved for the length of each said segment.

4. The apparatus according to claim 1, in which said detecting means includes means for detecting the resistance of the shape memory element.

5. The apparatus according to claim 4, in which said temperature adjusting means includes means for applying current pulses with a duty ratio corresponding to a difference between the target angle and the detected resistance to the shape memory element, and said resistance detecting means detects the resistance during the off period of the current pulse.

6. The apparatus according to claim 5, in which said current pulse is applied to the shape memory element by means of a first lead wire, and said resistance detecting means is connected to the shape memory element by means of a second lead wire.

7. The apparatus according to claim 6, in which said resistance detecting means is formed of a bridge circuit having the shape memory element as one side thereof.

8. The apparatus according to claim 1, in which the segment at the distal end of said probe is bendable within one plane, the other segments than said distal one being bendable within another plane perpendicular to said one plane; said input means inputs the bend angles of the distal-end segment and the segment next thereto; and said temperature adjusting means sets the inputted bend angles as the target bend angles for the distal-end segment and the next segment, and sets the detected bend angle of each segment subsequent to the distal-end segment as the target angle for each segment subsequent to the second segment, respectively.

9. The apparatus according to claim 1, in which said specific segment is the leading segment of the probe, and the detected bend angle of each segment is set as the target bend angle for each succeeding segment each time the probe is moved for half the length of each said segment.

10. The apparatus according to claim 1, in which said specific segment is the leading segment of the probe, and the detected bend angle of each segment is set as the target angle for each succeeding segment, when the probe is moved for half the length of each said segment, and whereupon the detected bend angle is set as the target bend angle each time the probe is moved for the length of each said segment.

11. The apparatus according to claim 1, in which the segments of said probe in odd numbers are bendable within one plane, and the segments in even numbers are bendable within a plane perpendicular to said one plane; said input means inputs the bend angles of the leading segment and the segment next thereto; and said temperature adjusting means sets the inputted bend angles as the target bend angles for the leading segment and the next segment, and sets the detected bend angle of the each segment as the target angle for succeeding segment by two.

12. The apparatus according to claim 1, in which said input means inputs the same angle for the leading segment and the segment next thereto and the detected bend angle of each of alternate pairs of segments, headed by the leading segment and the second segment, is set as the target angle for each subsequent pair of segments.

13. The apparatus according to claim 1, in which said detecting means includes conductive rubber means pasted on the shape memory element and adapted to change the resistance thereof as the rubber means is bent.

14. The apparatus according to claim 1, in which said detecting means includes a pressure-sensitive resistance element pasted on the shape memory element and adapted to change the resistance thereof as the resistance element is bent.

15. The apparatus according to claim 1, in which said detecting means includes a strain gage pasted on the shape memory element and adapted to change the resistance thereof as the strain gage is bent.

16. The apparatus according to claim 1, in which said temperature control means includes means for measuring the ambient temperature of the shape memory element and means for controlling the temperature of the shape memory element in accordance with the target bend angle and the measured temperature.

17. The apparatus according to claim 16, in which said temperature control means controls the temperature of the shape memory element within a range such that the linearity of the ambient temperature and the displacement characteristic of the shape memory element is satisfactory.

18. The apparatus according to claim 17, in which said temperature control means includes a heater disposed in the probe and adapted to keep the temperature of the shape memory element within the range for the satisfactory linearity of said characteristics.

19. The apparatus according to claim 1, in which said segments are arranged so that the ones nearer to the proximal end of the probe can bend more easily than the ones nearer to the distal end.

20. The apparatus according to claim 19, in which each said segment includes a bias spring for keeping the shape of the segment straight when the shape memory element is not bent, the diameter of a wire constituting said bias spring becoming greater with distance from the proximal end side.

21. The apparatus according to claim 19, in which each said segment includes a bias spring for keeping the shape of the segment straight when the shape memory element is not bent, the diameter of said bias spring becoming greater with distance from the distal end side.

22. The apparatus according to claim 19, in which each said segment includes a bias spring for keeping the shape of the segment straight when the shape memory element is not bent, the number of turns of said bias spring becoming greater with distance from the distal end side.

23. The apparatus according to claim 19, in which each said segment includes a bias spring for keeping the shape of the segment straight when the shape memory element is not bent, the modulus of elasticity of said bias spring becoming greater with distance from the distal end side.

24. The apparatus according to claim 1, in which said temperature adjusting means controls the amount of heat given to the shape memory element for the same target bend angle so that the heat amount becomes greater with distance from the distal end side.

25. The apparatus according to claim 24, in which said temperature adjusting means includes means for applying current pulses with a duty ratio corresponding to the target angle to the shape memory element, whereby the current pulses are controlled so that the amplitude of the pulses becomes greater with distance from the distal end side.

26. The apparatus according to claim 24, in which said temperature adjusting means includes means for applying current pulses with a duty ratio corresponding to the target angle to the shape memory element, whereby the current pulses are controlled so that the duty ratio of the pulses becomes greater with distance from the distal end side.

27. The apparatus according to claim 24, in which said temperature adjusting means includes means for applying current pulses, supplied with a bias signal in a duty ratio corresponding to the target angle, to the shape memory element, whereby the current pulses are controlled so that the value of the bias signal becomes greater with distance from the distal end side.

28. The apparatus according to claim 24, in which said temperature adjusting means includes means for applying current pulses with a duty ratio corresponding to the target angle to the shape memory element after an initial conduction period, whereby the current pulses are controlled so that the initial conduction period becomes longer with distance from the distal end side.

29. The apparatus according to claim 1, in which each said segment includes a bias spring for keeping the shape of the segment straight when the shape memory element is not bent, flanges attached individually to at least ends of the bias spring, and retaining members for fixing the shape memory element to the flanges.

30. The apparatus according to claim 29, in which said shape memory element is spiral in shape, and each said retaining member is formed of a pin or a screw fixed to the inner wall of a hole in the flange through the space between two adjacent turns of the shape memory element passed through the hole.

31. The apparatus according to claim 29, in which said shape memory element is spiral in shape, and each said retaining member is formed of a pin, a screw, or a plate fixed to the inner wall of a notch at the peripheral edge portion of the flange through the space between two adjacent turns of the shape memory element passed through the notch.

32. The apparatus according to claim 29, further comprising an intermediate flange located in the middle of said bias spring and holding the shape memory element free from displacement.

33. The apparatus according to claim 1, in which said shape memory element is plural or is formed of single shape memory means folded so as to be substantially plural, and each said segment includes a tube through which a cooling medium is circulated, said tube having knurls defining spaces for individually housing the shape memory elements.

34. The apparatus according to claim 1, in which the surface of said shape memory element is colored for good heat radiation.

35. The apparatus according to claim 1, in which each said shape memory element has indentations on the surface thereof.

36. An endoscopic apparatus comprising:
an endoscope body having a flexible insertion section containing an optical system for observation, the distal end of said insertion section being divided into a plurality of segments, each said segment including a shape memory element so that the segment bends as the shape memory element changes its shape;
means for inputting a target value of the bend angle for a specific segment;
means for detecting the distance of insertion of the insertion section;
means for detecting the bend angle of each said segment; and
means for heating the shape memory element by supplying a current thereto so that the bend angle of the shape memory element agrees with such a target angle that said inputted angle being set as the target angle for the specific segment, and said detected bend angle of each segment being set as the target angle for each succeeding segment and each said set value being renewed each time the insertion distance of the insertion section attains a predetermined distance.

37. The endoscopic apparatus according to claim 36, in which said endoscope body includes means for picking up an image obtained by means of the optical system for observation, said camera image being displayed on external display means.

* * * * *

UNITED STATES PATENT AND TRADEMARK OFFICE
CERTIFICATE OF CORRECTION

PATENT NO. : 4,930,494
DATED : June 5, 1990
INVENTOR(S) : TAKEHANA et al It is certified that error appears in the above-identified patent and that said Letters Patent is hereby corrected as shown below:

On the title page, under "Foreign Application Priority Data":

Change "63-73827(U)" to --63-73827--

Change "63-91093(U)" to --63-91093--

Change "63-91094(U)" to --63-91094--

Change "63-99040(U)" to --63-99040--

Change "63-136441(U)" to --63-136441--

Change "63-296803(U)" to --63-296803--

Change "63-150069" to --63-150069(U)--

Signed and Sealed this

Twenty-first Day of April, 1992

*Attest:*

HARRY F. MANBECK, JR.

*Attesting Officer*    *Commissioner of Patents and Trademarks*